(12) United States Patent
Salb

(10) Patent No.: US 6,226,352 B1
(45) Date of Patent: May 1, 2001

(54) SYSTEM AND METHOD FOR RADIOGRAPHIC IMAGING OF TISSUE

(75) Inventor: Jesse Salb, Los Angeles, CA (US)

(73) Assignee: Veritas Pharmaceuticals, Inc., Los Angeles, CA (US)

(*) Notice: Subject to any disclaimer, the term of this patent is extended or adjusted under 35 U.S.C. 154(b) by 0 days.

(21) Appl. No.: 09/149,734

(22) Filed: Sep. 8, 1998

(51) Int. Cl.[7] ............... G01F 1/66; G01N 23/04; G05G 1/64; H01J 35/08

(52) U.S. Cl. ............... 378/98.9; 378/51; 378/62; 378/143

(58) Field of Search ............... 378/98.9, 51, 62, 378/143

(56) References Cited

U.S. PATENT DOCUMENTS

| | | | |
|---|---|---|---|
| 3,701,771 | 10/1972 | Almen et al. | 260/211 R |
| 3,854,049 | 12/1974 | Mistretta et al. | 250/402 |
| 3,974,386 | 8/1976 | Mistretta et al. | 250/402 |
| 4,243,653 | 1/1981 | Sovak et al. | 424/5 |
| 4,250,113 | 2/1981 | Nordal et al. | 564/153 |

(List continued on next page.)

FOREIGN PATENT DOCUMENTS

| | | |
|---|---|---|
| 0 270 340 | 6/1988 | (EP). |
| WO 98/57669 | 12/1998 | (WO). |

OTHER PUBLICATIONS

PCT International Search Report for PCT Int'l Appln No. PCT/US99/20298 mailed Apr. 25, 2000 (7 pages).

(List continued on next page.)

*Primary Examiner*—Frank G. Font
*Assistant Examiner*—Armando Rodriguez
(74) *Attorney, Agent, or Firm*—Blakely, Sokoloff, Taylor & Zafman

(57) ABSTRACT

System and method for radiographic imaging of tissue using a non-radioactive, radio-opaque imaging agent that accumulates intracellularly in tissue in proportion to its functional, or physiological, activity. In one embodiment, the imaging agent is a cell-membrane permeable, radio-opaque, high affinity ligand for the intracellular enzyme hexokinase. The imaging agent is administered to a patient, and after an accumulation interval, radiographic images are acquired. The imaging agent preferentially accumulates in malignant tissue and increases its radio-opacity because of its elevated glucose metabolic rate relative to benign and normal tissue. The tissue being examined is transilluminated by X-ray beams with preselected different mean energy spectra, and a separate radiographic image is acquired during transillumination by each beam. An image processing system performs a weighted combination of the acquired images to produce a single displayed image. The image processing procedure isolates the radiographic density contributed solely by differential accumulation of the imaging agent in malignant, benign, and normal tissue. The system and method thus provides a functional image displayed with the anatomical detail and spatial resolution of a radiographic image. The viewer may interactively control the relative proportion of radiographic density contributed by imaging agent, soft tissue, and bone to the displayed image, allowing the display of functional and anatomical information in complete registration, and facilitating localization of malignant tissue in relation to nearby anatomical structures. In other embodiments, the system and method may be used to detect enzymes, nucleic acids, coenzymes, fatty acids, and other cellular targets in diagnostic imaging applications.

77 Claims, 10 Drawing Sheets

U.S. PATENT DOCUMENTS

| | | | |
|---|---|---|---|
| 4,364,921 | 12/1982 | Speck et al. | 424/5 |
| 4,455,292 | 6/1984 | Bertoni | 424/5 |
| 4,716,225 | 12/1987 | Ledley et al. | 536/122 |
| 4,887,604 * | 12/1989 | Shefer et al. | 128/654 |
| 5,093,042 | 3/1992 | Counsell et al. | 260/408 |
| 5,141,739 | 8/1992 | Jung et al. | 424/4 |
| 5,198,977 | 3/1993 | Salb | 364/413.01 |
| 5,408,996 | 4/1995 | Salb | 128/633 |
| 5,466,786 | 11/1995 | Buhr et al. | 536/26.26 |
| 5,610,289 | 3/1997 | Cook et al. | 536/25.34 |
| 5,728,527 | 3/1998 | Singer et al. | 435/6 |
| 5,729,620 | 3/1998 | Wang | 382/128 |
| 5,763,208 | 6/1998 | Bischofberger et al. | 435/40.5 |
| 6,071,491 * | 6/2000 | Epstein et al. | 424/1.49 |

OTHER PUBLICATIONS

Bech L. et al., "Metabolic effect of topical application of metrizamide to rat brain cortex," Acta Neurol. Scand. vol. 72 pp. 427–431 (1985).

Guidolet J. et al., "Cardiovascular radiology. Subcellular localization of uro–angiographic contrast by 125I–labeled media," Invest. Radiol. vol. 15 pp. S215–S219 (Nov.–Dec. 1980).

Nordby A. et al., "Intracellular penetration and accumulation of radiographic contrast media in the rat kidney" (and discussion), Scanning Microsc. 4:3 pp. 651–666 (1990).

Nordby A. et al., "Incorporation of contrast media in cultured cells," Invest Radiol. vol. 24 pp. 703–710 (Sep. 1989).

Nordby A. et al., "Effects on the ATP content of cultured cells after radiographic contrast media exposure. Evidence for accumulation of contrast media in cultured cells," Acta Radiol. vol. 30 pp. 541–547 (1989).

Nordby A. et al., "Short–term effects of radiographic contrast media on monolayer cell cultures and hepatocytes," Invest. Radiol. vol. 22 pp. 603–607 (Jul. 1987).

Norby A. et al., "Effects of radiographic contrast media on monolayer cell cultures," Invest. Radiol. vol. 21 pp. 234–239 (Mar. 1986).

Weichert J.P. et al., "Polyiodinated triglyceride analogs as potential computed tomography imaging agents for the liver," J. Med. Chem. vol. 38 No. 4 pp. 636–646 (1995).

Agrawal S. et al., "Pharmacokinetics of oligonucleotides", Ciba Foundation Symposium 209, pp. 60–78 (1997).

Aleshin A.E. et al., "The mechanism of regulation of hexokinase: new insights from the crystal structure of recombinant human brain hexokinase complexed with glucose and glucose–6–phosphate", Structure 6(1):39–50 (1998).

Aller C.B. et al., "Flow cytometric analysis of glucose transport by rat brain cells", Cytometry 27:262–268 (1997).

Alpert N.M. et al., "Improved methods for image registration", Neuroimage 3:10–18 (1996).

Arora K.K. et al., "Functional significance of mitochondrial bound hexokinase in tumor cell metabolism. Evidence for preferential phosphorylation of glucose by intramitochondrially generated ATP", J. Biol. Chem. 263(33):17422–17428 (Nov. 25, 1998).

Barnett J.E.G. et al., "Structural requirements for binding to the sugar–transport system of the human erythrocyte", Biochem. J. 131:211–221 (1973).

Barnett J.E.G. et al., "Evidence for two asymmetric conformational states in the human erythrocyte sugar–transport system", Biochem. J. 145:417–429 (1975).

Dewanjee M.K. et al., "Noninvasive imaging of c–myc oncogene messenger RNA with indium–111–antisense probes in a mammary tumor–bearing mouse model", J. Nuc. Med. 35(6):1054–1063 (1994).

Eisenhut M. et al., "Trapping and metabolism of radioiodinated PHIPA 3–10 in the rat myocardium", J. Nucl. Med. 38(12):1864–1869 (1997).

Ekholm S.E. et al., "Neural tissue uptake and clearance of iohexol following lumbar myelography in rabbits", Acta Radiologica Diagnosis (Stockh). 26:331–336 (1985).

Elmore J.G. et al., "Ten–year risk of false positive screening mammograms and clinical breast examinations", N. Eng. J. Med. 338(16):1089–1096 (1998).

Friston K.J. et al., "Spatial registration and normalization of images", Human Brain Mapping 2:165–189 (1995).

Ghose A.K. et al., "Atomic physiochemical parameters for three dimensional structure directed quantitative structure–activity relationships III: Modeling hydrophobic interations", J. Comp. Chem. 9(1):80–90 (1988).

Gjedde A.: "The blood–brain barrier is impermeable to metrizamide", Acta Neurol. Scandinav. 66:392–395 (1982).

Golman K.: "Distribution and retention of 125I–labeled metrizamide after intravenous and suboccipital injection in rabbit, rat, and cat", Acta Radiol. Suppl. S335:300–311 (1973).

Hansch C. et al., "Linear relationships between lipophilic character and biological activity of drugs", J. Pharm. Sci. 61(1):1–19 (Jan. 1972).

Hansch C. et al., "Exploring QSAR: fundamentals and applications in chemistry and biology", pp. 97–168, Amer. Chem. Soc., Washington, DC (1995).

Henry C. et al., "[123I]–6–deoxy–6–iodo–D–glucose (6DIG).: a potential tracer of glucose transport", Nuc. Med. Biol. 24:527–534 (1997).

Hoh C.K. et al., "Pet in oncology: will it replace the other modalities?", Seminars in Nuc. Med. 27(2):94–106 (Apr. 1997).

Hosokawa R., et al., "Myocardial kinetics of Iodine–123–BMIPP in canine myocardium after regional ischemia and reperfusion: implications for clinical SPECT", J. Nucl. Med. 38:1857–1863 (1997).

Kamp F. et al., "Fatty acid flip–flop in phospholipid bilayers is extremely fast", Biochemistry 34:11928–11937 (1995).

Kamp F. et al., "Movement of fatty acids, fatty acid analogues, and bile acids across phospholipid bilayers", Biochemistry 32:11074–11086 (1993).

Kelcz F. et al., "Spectral considerations for absorption–edge fluoroscopy", Medical Physics 4(1):26–35 (Jan./Feb. 1977).

Kelcz F. et al., "Absorption–edge fluoroscopy using a three–spectrum technique", Medical Physics 3(3):159–168 (May/Jun. 1976).

Keller T.H. et al., Synthesis and hybridization properties of oligonucleotides containing 2'–O–modified ribonucleotides, Nucleic Acids Res. 21(19):4499–4505 (1993).

Kormano M. et al., "Toxicity of X–ray contrast media in cell cultures", Invest. Radiol. 15:68–71 (1980).

Loke S.L. et al., "Characterization of oligonucleotide transport into living cells", Proc. Natl. Acad. Sci. USA 86:3474–3478 (1989).

Machulla H.J. et al. "Comparative evaluation of fatty acids labeled with C–11, Cl–34m, Br–77, and I–123 for metabolic studies of the myocardium: concise communication", J. Nucl. Med. 19:298–302 (1978).

Macovski A. et al., "Isolated iodine images using spatial–frequency encoding", *Med. Phys.* 6(1):53–58 (Jan./Feb. 1979).

Maley F. et al., "Synthesis of N–substituted glucosamines and their effect on hexokinase", *J Biol. Chem.* 214:765–773 (1955).

Matteucci M., "Oligonucleotide analogues: an overview", *Ciba Foundation Symposium 209*, pp. 5–18 (1997).

Meylan W.M., "Atom/fragment contribution method for estimating octanol–water partition coefficients", *J. Pharm. Sci.* 84(1):83–92 (1995).

Mueckler M., "Facilitative glucose transporters", *Eur. J. Biochem.* 219:713–725 (1994).

Nelson C.A. et al., "Targeting of glucose transport proteins for tumor imaging: is it feasible?", *J. Nucl. Med* 37:1031–1037 (1996).

Railton R. et al., "Myocardial scintigraphy with 1–123 heptadecanoic acid as a test for coronary heart disease", *Euro. J. Nucl. Med* 13:63–66 (1987).

Rekker, R.F. et al., "Calculation of Drug Lipophilicity," VCH, Weinheim, pp. 1–43 (1992).

Riederer S.J. et al., "Three–beam K–edge imaging of iodine using differences between fluoroscopic video images: theoretical considerations", *Med. Phys.* 8(4):471–479 (Jul./Aug. 1981).

Riederer S.J. et al., "Three–Beam K–edge imaging of iodine using differences between fluoroscopic video images: experimental results", *Med. Phys.* 8(4):480–487 (Jul./Aug. 1981).

Ries L.A.G. et al. (eds).: "Surveillance, Epidemiology, and End Results Program, 1998," *SEER Cancer Statistics Review*, 1973–1995, National Cnacer Institute, 42 pp. (1998).

Sols A. et al., "Substrate specificity of brain hexokinase", *J. Biol. Chem.* 210:581–595 (1954).

Speck U., "Basic pharmacology of iodinated contrast media", *Contrast Media*, pp. 1–13. Churchill Livingstone, NY (1988).

St. Charles R. et al., "Molecular model of human beta–cell glucokinase built by analogy to the crystal structure of yeast hexokinase B", *Diabetes* 43:784–791 (1994).

Tavitian B. et al., "In vivo imaging of oligonucleotides with positron emission tomography", *Nature Medicine* 4(4):467–471 (1998).

Torikuza K. et al., "A Phase 1 study of beta–methyl–p–(123l)–iodophenyl–pentadecanoic acid (123l–BMIPP)", *Jpn. J. Nucl. Med.* 28:681–690 (1991).

Trigatti B.L. et al., "The effect of intracellular pH on long–chain fatty acid uptake in 3T3–L1 adipocytes: evidence that uptake involves the passive diffusion of protonated long–chain fatty acids across the plasma membrane", *Biochem. J.* 313:487–494 (1996).

van Dijck J.A. et al., "The current detectability of breast cancer in a mammographic screening program. A review of the previous mammograms of interval and screen–detected cancers", *Cancer* 72(6):1933–1938 (Sep. 15, 1993).

Van Eenige M.J. et al., "Clinical value of studies with radioiodinated heptadecanoic acid in patients with coronary artery disease", *Eur. Heart J.* 11:258–268 (1990).

Wallis M.G. et al., "A review of false negative mammography in a symptomatic population", *Clin. Radiol.* 44:13–15 (1991).

Weber G., "Molecular correlation concept: ordered pattern of gene expression in neoplasia", *GANN Monograph on Cancer Res.* 13:47–77 (1972).

Weinhouse S., "Glycolysis, respiration, and anomalous gene expression in experimental hepatomas", *Cancer Res.* 32(10):2007–2016 (1972).

Willson M. et al., "Yeast hexokinase inhibitors designed from the 3–D enzyme structure rebuilding", *J. Enz. Inhib.* 12:101–121 (1997).

Woods R.P. et al., "Automated image registration: I. General methods and intrasubject, intramodality validation", *J. Comput. Assist. Tomogr.* 22(1):139–152 (1998).

Woods R.P. et al., "Automated image registration: II. Intersubject validation of linear and nonlinear models", *J. Comput. Assist. Tomogr.* 22(1):153–165 (1998).

Woods R.P. et al., "MRI–PET registration with automated algorithm", *J. Comput. Assist. Tomogr.* 17(4):536–546 (Jul./Aug. 1993).

* cited by examiner

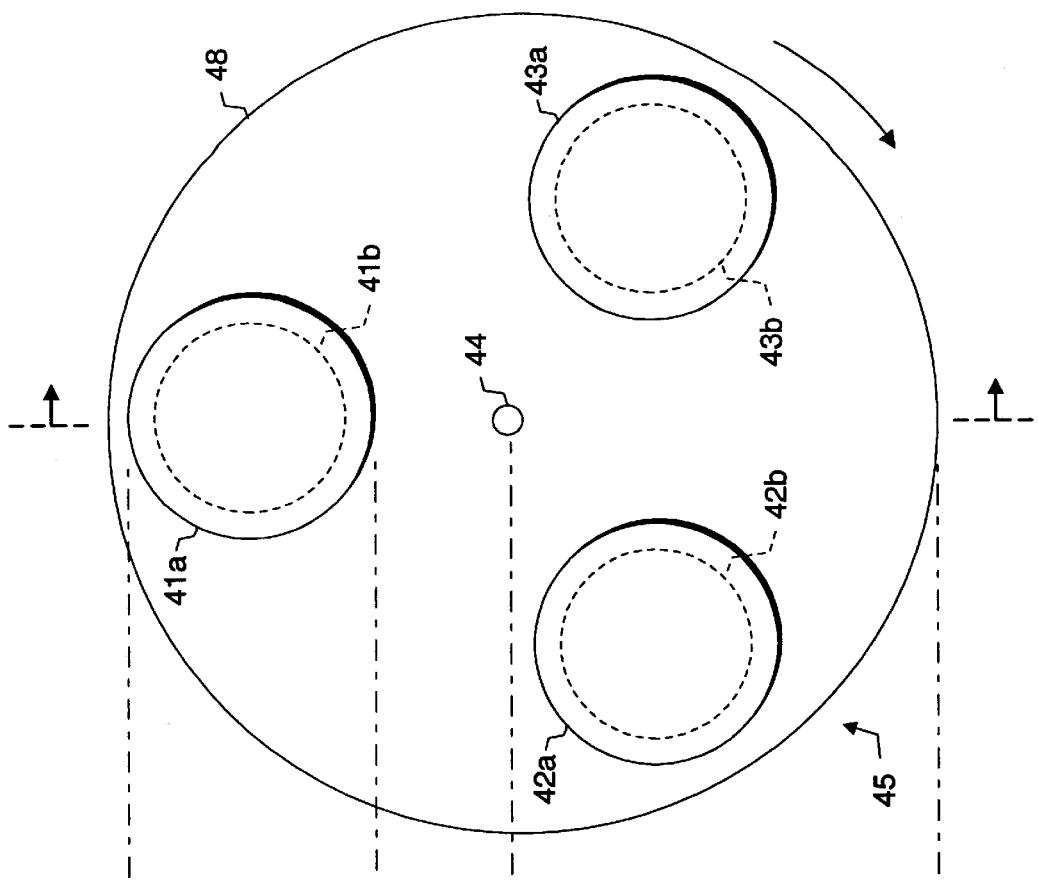
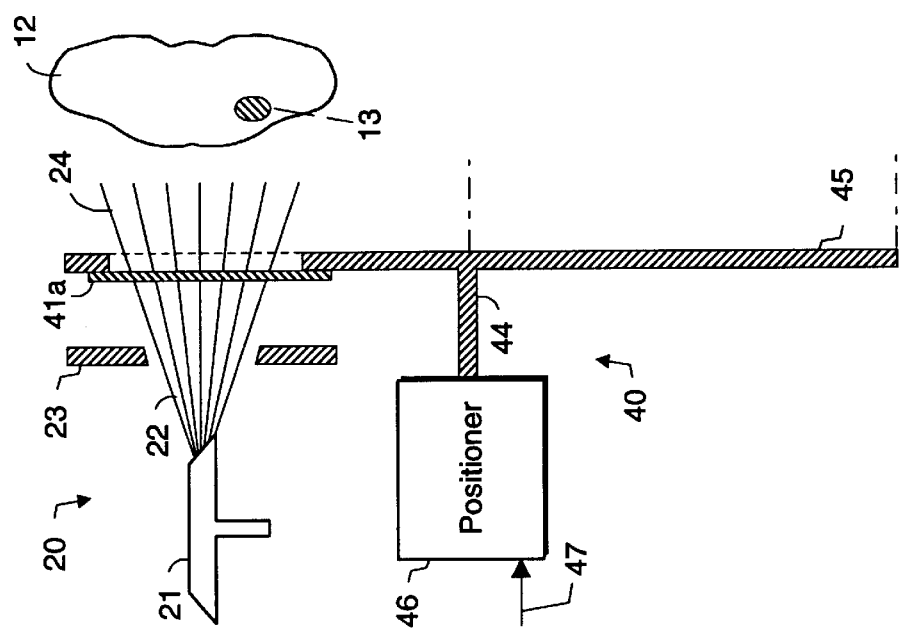

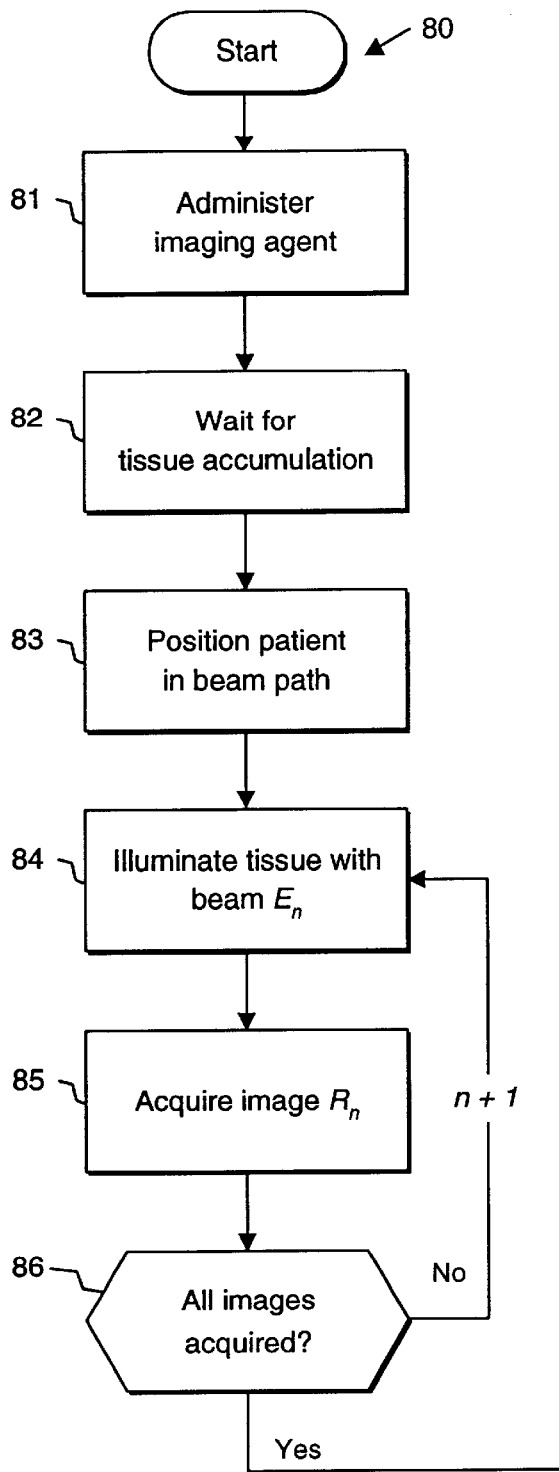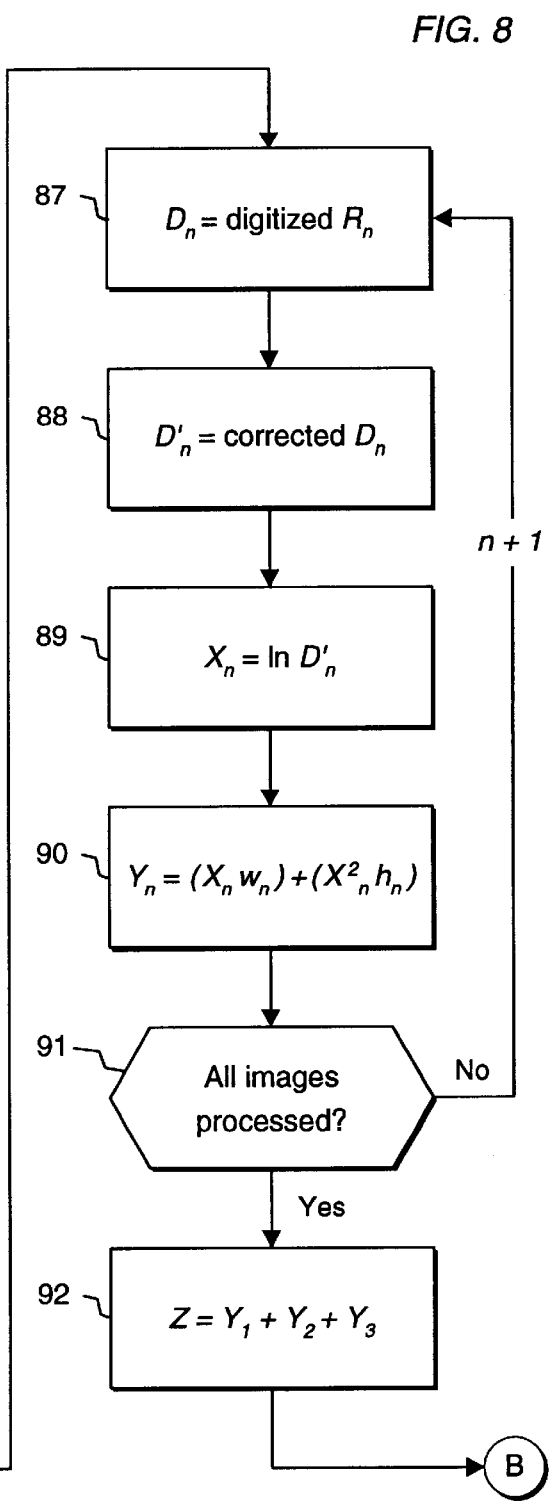
FIG. 8

SYSTEM AND METHOD FOR RADIOGRAPHIC IMAGING OF TISSUE

BACKGROUND OF THE INVENTION

A. Field of the Invention

This invention relates to medical imaging and specifically to a system and method for localization of certain types of abnormal tissue, such as malignant tissue, using radiography.

B. Description of the Related Art

Radiography involves examination of internal organs of the body by transillumination with X-rays. The image receptor may be radiographic film, a film/intensifying screen combination, a stimulable phosphor storage plate, a fluoroscopic image intensifier, an amorphous silicon sensor array, a CCD/scintillator combination, or another type of X-ray sensitive receptor. In digital radiography, a computer digitizes the acquired image and may enhance it using image processing algorithms. The most commonly performed radiographic procedures include mammography, in which images of the breast are generated to detect breast cancer, and thoracic radiography, in which images of the lungs and heart are generated to detect a variety of diseases, including lung cancer.

A major goal of radiography is the reliable detection of malignant tissue and its accurate differentiation from non-malignant tissue. In current practice, the radiologist decides whether tissue is malignant, benign or normal solely by visual inspection of the radiograph The appearance of tissue on a radiograph mainly depends on the degree to which the transilluminating X-ray beam is attenuated during its traversal of the different areas of the tissue being examined. However, it has been repeatedly demonstrated that the visual appearance of tissue on the radiograph is not a reliable criterion for definitive diagnosis of malignancy.

Studies confirm a high error rate in the radiological diagnosis of cancer. These errors fall into two categories: false positives and false negatives. A false positive, also called an error in specificity, occurs when a radiograph is judged to display malignant tissue that ultimately proves benign. A false negative, also called an error in sensitivity, occurs when malignant tissue actually present is not detected on the radiograph.

One of the most commonly performed radiographic procedures is mammography, in which the breasts are examined for evidence of cancer. Approximately 25 million primary screening mammograms are performed annually in the United States. However, the high incidence of false positives and false negatives reduces the reliability of mammography as a diagnostic tool.

The major sources of false positives on mammograms are cysts and fibroadenomas. Cysts are benign fluid-filled tissue structures that may often be present in an otherwise normal breast. Fibroadenomas are benign growths of tissue that may also be present in a normal breast. Both types of structures may feel lumpy during palpation by the patient or a physician, and may thus resemble malignant tumors in a physical examination. In addition, both cysts and fibroadenomas appear as areas of decreased radiographic density on mammograms. Their radiographic appearance can closely resemble that of malignant tumors, which also appear as areas of decreased density.

According to various published studies, between 6% and 13% of primary screening mammograms manifest radiographic evidence of possible malignancy, but of these positive or suspicious results, approximately 80% are ultimately diagnosed as benign [Elmore J G et al.: N. Eng. J. Med. 338: 1089–1096 (1998)]. However, as previously noted, it is currently impossible to reliably differentiate malignant from benign tissue solely by visual inspection of the mammogram. Consequently, the majority of patients with positive primary results require further diagnostic procedures, including additional mammograms and excisional (surgical) or needle biopsies. Secondary diagnostic workups that include biopsies usually cost between $1500–3000. In addition to increased cost, biopsies carry the risk of infection, scarring, pain, and anxiety.

Thus, a method for more accurate differentiation of malignant tissue from benign and normal tissue on mammograms would eliminate the need for many of the biopsies now performed, decreasing procedure cost and patient morbidity.

A more serious problem in diagnostic mammography is the high incidence of false negatives, in which malignant tumors that are actually present are not detected on the mammogram. Missed tumors may be detected months or years later on a subsequent mammogram or by palpation. During this interval the tumor may grow larger and, in the worst case, metastasize. Various published studies on diagnostic accuracy in mammography report a false negative rate of between 8% and 24% [van Dijck J A et al.: Cancer 72: 1933–1938 (1993); Bird R E et al.: Radiol. 184: 613–617 (1992); Wallis M G et al.: Clin. Radiol. 44: 13–15 (1991)]. Particularly in their early stages of development, malignant tumors may not be noticed even upon careful inspection of the mammogram by an experienced radiologist. Tumors may be too small to be detected, or their appearance may be obscured by benign tumors or cysts. The visibility of malignant tumors may be further obscured in younger women, whose breast tissue is often dense. As a consequence, the rate of false negatives in these women is even higher than in the general population.

It has reliably been demonstrated that the stage at which malignant breast tumors are detected is an important determinant of the effectiveness of therapy and of the patient's survival time. [Ries L A G et al. (eds): SEER Cancer Statistics Review, 1973–1995, National Cancer Institute (1998)].

The high incidence of missed cancers on mammograms suggests that there is a minimum size threshold for detection of malignant tumors using current radiographic methods, and that these tumors may be present in the body long before they are detected.

Thus, an improved method for visualization of small malignant tumors on mammograms would enable their earlier detection, enhance the effectiveness of therapy, and prolong patient survival time.

Similar diagnostic problems are common in thoracic radiography, in which radiographic imaging of the lungs and heart is performed to detect abnormal tissue, particularly malignant tumors. Over 16 million thoracic radiographs are performed annually in the United States. Approximately 3 of every 100 thoracic radiographs show evidence of small isolated masses in the lung. Approximately 50% of these masses, known as solitary pulmonary nodules, are benign. However, it is impossible to reliably differentiate malignant nodules from benign nodules solely by inspection of the radiograph. Definitive diagnosis of these nodules currently requires surgical resection or invasive biopsy. As in the case of breast biopsies, these procedures are expensive and add patient morbidity risk.

Thus, an improved method for differentiation of malignant tissue from benign and normal tissue on thoracic radiographs would reduce the large number of unnecessary follow-up procedures currently performed, decreasing cost and morbidity.

As in the case of mammography, false negatives in thoracic radiography lead to less effective therapy and shorter patient survival time. Particularly in their early stages of development, malignant lung tumors may not be detected even upon careful inspection of the radiograph. The early detection of lung cancer is of particular importance because the overall survival rate from the disease is very low. It has been repeatedly shown that the survival time of patients whose lung tumors are detected at an early stage in their development is much longer than that of patients whose tumors are detected in later stages [Ries L A G et al. (eds): SEER Cancer Statistics Review, 1973–1995, National Cancer Institute (1998)].

Thus, an improved method for visualization of small malignant lung tumors on thoracic radiographs would enable earlier detection of these tumors and prolong patient survival time.

Recognition of the current inadequacies of the radiographic art has led to attempts to develop more accurate methods for diagnostic imaging of cancer.

One commonly pursued approach to the improvement of diagnostic accuracy has been to increase the spatial resolution of radiographic imaging devices. Radiographs with higher spatial resolution improve the ability of the radiologist to visualize fine anatomical detail. However, this approach is fundamentally flawed because detection of malignant tissue, even in high-resolution images, still largely depends on variations in radiographic density. But, as previously noted, radiographic density alone is not a reliable criterion for detection of malignant tissue. Improved spatial resolution can therefore result in only a modest improvement in diagnostic accuracy.

A more successful approach to the improvement of diagnostic accuracy is based on generating images of tissue glucose metabolism using positron emission tomography (PET). These images, which measure physiological function, are referred to as functional images, in contrast to the anatomical images generated by most other commonly used imaging modalities. PET functional imaging exploits the fact that the glucose metabolic rate of malignant tissue is considerably elevated relative to that of benign and normal tissue in the same organ. In a PET scan, a positron-emitting radioactive glucose analog, typically $^{18}$F-2-fluoro-2-deoxyglucose, is administered to the patient. After an interval of approximately one hour, images of the distribution of the radioactive glucose analog in body tissue are acquired by a photon detector array that surrounds the patient. In direct comparisons with anatomical imaging modalities, including computed tomography, magnetic resonance imaging, and ultrasound, PET functional images of tissue glucose metabolism have repeatedly proven more sensitive and specific in the detection of malignant tumors, particularly those larger than 1 cm. [Hoh C K et al.: Semin. Nuc. Med. 27: 94–106 (1997); Conti P S et al.: Nuc. Med. Biol. 23: 717–735 (1996)]

The most formidable barrier to the use of PET is its cost. A cyclotron is required to generate the positron-emitting radiopharmaceuticals required in the imaging procedure, and a complex detector array is required to detect photon emission. Capital equipment costs of the imaging device and cyclotron are very high. In addition, radiochemists are needed to perform complex syntheses of radiopharmaceuticals whose half-lives are typically 2 hours. Because of the high capital equipment, materials, and labor costs, the cost of a PET scan to the patient is approximately $2500. Because of its prohibitive cost, PET imaging is not widely available, and is not likely to be used in the foreseeable future for routine cancer diagnosis.

A second disadvantage of PET is the lower spatial resolution of PET images compared to those generated by radiography. Relatively low spatial resolution is a limitation common to imaging modalities that depend on detector arrays for the measurement of high-energy particles emitted from radiopharmaceuticals. Because of its low spatial resolution, PET exhibits a high rate of false negatives in the detection of small malignant tumors.

A third disadvantage of PET is the length of the imaging procedure. The time required for a patient to be immobile during a PET scan may be one-half to one hour, while radiographic images can be acquired in a few minutes.

Another approach to the improved detection of malignant tissue has been the development of single-photon emission computed tomography (SPECT). In this imaging modality, a photon-emitting radiopharmaceutical is administered to the patient. After an interval during which the radioactive imaging agent accumulates in body tissue, images are acquired using a gamma camera. The gamma camera detects photons emitted by the imaging agent.

The most common radiopharmaceutical used in SPECT imaging of malignant tissue is Tc-99m-Sestamibi. Results of a number of studies have shown selective uptake of Tc-99m-Sestamibi in malignant tumors of various types.

Nevertheless, SPECT imaging has limitations that reduce its utility in the diagnosis of malignant tumors. In the diagnosis of breast cancer, a major limitation of the technique is the low spatial resolution of the images, which results in a sharp decrease in sensitivity for breast tumors smaller than 1.5 cm. By the time tumors have grown to this size, they are almost always palpable in physical examination by the patient or the physician, and may have advanced to a late stage in their development.

A second disadvantage of SPECT in breast cancer imaging is the relatively low specificity. In particular, Tc-99m-Sestamibi produces a significant number of false positives in patients with benign fibroadenomas. Since fibroadenomas constitute the most frequent source of false positives, and frequently result in unnecessary biopsies, the large number of false positives produced by Tc-99m-Sestamibi reduces its value in breast cancer imaging. In diagnostic imaging of the lung, SPECT generates false positives in conditions such as tuberculosis, pneumonia, and granulomas. It is thus inadequate for the reliable diagnosis of lung cancer.

Other imaging modalities, including computed tomography (CT), magnetic resonance imaging (MRI), and ultrasound, are also used for diagnosis of malignant tumors, with varying degrees of success. However, over the past 15 years, clinical studies have repeatedly demonstrated that PET functional imaging of tissue glucose metabolism is the most accurate modality now available for the detection of malignant tissue.

A wide variety of contrast agents have also developed to enhance the delineation of tissue on radiographic images [Torsten et al.: U.S. Pat. No. 3,701,771; Speck et al.: U.S. Pat. No. 4,364,921; Nordal et al.: U.S. Pat. No. 4,250,113; Sovak et al.: U.S. Pat. No. 4,243,653]. However, almost all commonly used radiographic contrast agents function by passively outlining body organs and structures, thereby enhancing anatomical contrast on the radiograph. These imaging agents generally accumulate in the extracellular space. Commonly used radiographic contrast agents are hydrophilic, and are therefore not cell-membrane permeable [Speck U: Contrast Media pp. 1–23. Churchill Livingstone, New York (1988)]. Studies of tissue distribution at the cellular level confirm that commonly used radiographic contrast agents, such as metrizamide, iohexol, and meglumine calcium metrizoate, do not permeate the cell membrane nor enter the intracellular cytosol. [Golman K: Acta Radiol. Suppl. S335: 300–311 (1973); Ekholm S E et al.: Acta Radiol. [Diagn] (Stockh) 26: 331–336 (1985); Gjedde A: Acta Neurol. Scandinav. 66: 392–395 (1982); Kormano M, Frey H: Invest. Radiol. 15: 68–71 (1980)]. Because these contrast agents do not enter the cytosol, they do not specifically interact with intracellular targets, and therefore cannot be used to provide images which contain information on intracellular function or physiology. The utility of these radiographic contrast agents in the detection of functionally abnormal tissue is thereby limited.

Certain radiographic contrast agents have been developed which do enter and exit cells. However, in each instance, disadvantages associated with the mechanisms of cellular entry and exit of the molecules preclude their use in the diagnostic imaging applications addressed by the present invention.

Jung et al. (U.S. Pat. No. 5,141,739) disclosed a method of targeting X-ray contrast agents to a particular population of cells using a complex of a radio-opaque label and a polysaccharide. These contrast agents, whose major application is in the enhancement of CT images of the liver, enter cells through the mechanism of receptor-mediated endocytosis (RME). In this mode of delivery, contrast agent molecules attach to receptors on the cell surface and are internalized into the cell through pinching off of the cell membrane to form intracellular vesicles. Although these RME-based contrast agent molecules are physically localized within the cell, they are separated from the cytosol by the cell membrane surrounding the vesicle. Since the contrast agent molecules are not cell membrane-permeable, they cannot exit the vesicles which enclose them. They therefore have no direct access to the cytosol, and consequently do not specifically interact with, or bind to, intracellular targets. Similar contrast agents have been designed to enhance radiographic images of the liver by entering hepatocytes. As in the example cited above, molecules of these contrast agents are physically localized within the cell, but are compartmentalized within liposomes or intracellular vesicles. They are thus separated from the cytosol by the membrane barrier surrounding the liposome or vesicle. Since the molecules are not membrane-permeable, they do not have direct access to the cytosol and do not specifically interact with intracellular targets.

Ledley and Gersten (U.S. Pat. No. 4,716,225) disclosed a method of metabolic mapping of the central nervous system using iodinated sugar derivatives. The sugar derivatives are hexoses substituted with iodine atoms in either the C-2, C-5, or C-6 positions. Patterns of metabolism are mapped using CT scans to generate images of the concentration flux of the radio-opaque sugars in different areas of tissue in the central nervous system. The concentration flux is a measurement which reflects the rate of uptake of the compounds by cells.

The disclosed radio-opaque sugar derivatives are hydrophilic, and enter cells only via facilitated transport by the glucose transport (GLUT) proteins. Because the radio-opaque sugar derivatives are iodine-substituted in different ring positions, their interaction with the GLUT proteins differ from the interaction of native hexoses with these proteins. The binding requirements of the GLUT proteins are asymmetrical, and depend on which side of the cell membrane the sugar ligand is located. [Mueckler M: Eur. J. Biochem. 219: 713–725 (1994); Barnett J E G et al.: Biochem. J. 131: 211–221 (1973); Barnett J E G et al.: Biochem. J. 145: 417–429 (1975); Colville C A et al.: Biochem. J. 294: 753–760 (1993)]. Thus, it was reported that the disclosed molecules were able to enter cells, but once inside, were unable to freely exit. The compounds were shown to be present in tissue at higher concentrations 9 days after administration than 1 hour after administration. These figures indicate that the disclosed molecules had very slow rates of cellular uptake and elimination. The very slow rates of cellular entry and exit render these molecules of limited value in diagnostic imaging procedures. It is apparent that these molecules are not bidirectionally cell membrane permeable.

In addition, it has been demonstrated that the rate of glucose transport and expression of GLUT proteins in malignant tissue are not consistently abnormal relative to normal tissue. This inconsistency minimizes the utility of glucose transport as a diagnostic criterion for the detection of malignant tissue. [Nelson C A et al.: J. Nucl. Med 37: 1031–1037 (1996); Binder C et al.: Anticancer Res 17: 4299–4304 (1997)].

In order to improve the diagnostic utility of space-filling radiographic contrast agents, methods have been developed to enhance their visualization in the body. Mistretta et al. (U.S. Pat. No. 3,854,049; U.S. Pat. No. 3,974,386) described the use of multiple X-ray beams to enhance visualization of iodinated contrast agents in fluoroscopic imaging and to cancel the contribution of radiographic density of soft tissue and bone to the image. Another method isolated images of an iodinated contrast agent in the presence of tissue using spatial frequency encoding on a radiographic image [Macovski A et al.: Med. Phys 6: 53–58 (1979)]. These methods were directed solely to the visualization of extracellular, space-filling radiographic contrast agents. It was not suggested that cell membrane-permeable, intracellularly localized radiographic contrast agents might be imaged using these methods, as no such imaging agents were available or known at the time. In addition, these methods did not provide the capability of generating functional physiological images of body tissue, nor of presenting a visually aligned combination of a functional and an anatomical image of the same tissue.

A radiographic imaging agent that facilitated generation of functional physiological images in addition to the anatomical images now provided by radiographs, and which could be used with widely available radiographic imaging devices, would be of great value in the practice of radiography, particularly in the diagnostic imaging of cancer. This capability is not currently provided by any radiographic contrast agent.

In addition, the simultaneous display of functional images and anatomical images of high resolution, with both images superimposed in registration, is highly desirable for diagnostic and research purposes in medical imaging. Registration refers to the exact visual alignment, or superimposition, of two or more images from the user's viewpoint. Further, the capability of interactively varying the proportions of the displayed functional and anatomical information on a single image with complete registration would also be of great value. With this capability, for example, areas of abnormal functional (physiological) activity might be correlated with nearby anatomical landmarks, and either the anatomical or functional image might be emphasized. These capabilities would enhance the ability of the physician to precisely localize areas of abnormal tissue such as malignant tumors. These capabilities are not provided by any currently available single imaging modality.

Many approaches to the need for the simultaneous display and registration of functional and anatomical images have been developed [Woods et al.: J. Computer Assisted Tomogr. 22: 139–152 (1998); Alpert N M et al.: Neuroimage 3: 10–18 (1996); Friston et al.: Hum Brain Map. 2:165–189 (1995); Woods et al.: J. Comput. Assisted Tomogr. 17: 535–546 (1993)]. These methods of image display and registration all require the use of separate anatomical and functional imaging devices, such as PET and MRI, to sequentially acquire images of the patient during separate imaging procedures. The acquired image data arrays are later combined using software algorithms. These software computations are generally time-consuming and require considerable computational hardware.

Wang (U.S. Pat. No. 5,729,620) disclosed a system for superimposing digitized images representing X-ray data in registration with an annotation map. The annotation map may be constructed by a computer-aided diagnosis (CAD) system. The invention does not suggest a method of superimposing anatomical images in registration with functional (physiological) images of tissue, as CAD systems do not provide functional images.

It is thus evident that the present state of the diagnostic imaging art does not provide a sufficiently accurate, inexpensive, and widely available modality for detection and localization of certain types of tissue such as malignant tissue. An ideal imaging modality should combine the proven diagnostic accuracy of functional imaging of tissue physiology with the high anatomical resolution of radiography. It may also provide the ability to display functional and anatomical information on a single image with complete registration. An imaging modality with these characteristics should improve detection of small tumors at an earlier stage in their development, and improve differentiation of malignant from non-malignant tissue. Both false negative and false positive errors should thereby be reduced. The diagnostic imaging of other types of abnormal tissue should also be improved. The ideal imaging modality should also provide low-cost images, improve the accuracy of currently installed radiographic imaging devices, and not require the use of radiopharmaceuticals. An imaging modality providing these advantages should satisfy an urgent need in the practice of diagnostic imaging.

SUMMARY OF THE INVENTION

The present invention is a system and method for improved detection and localization of abnormal or diseased tissue, such as malignant tissue, using radiography. The present invention provides the capability of generating a radiographic image of tissue that combines both functional (physiological) and anatomical information on a single image with the two types of information in complete spatial registration. The present invention also allows the viewer to interactively control the relative proportions of functional and anatomical information presented on the displayed image. This capability facilitates the precise localization of certain types of tissue, such as functionally abnormal malignant tissue, in relation to anatomical structures.

Because of these improvements and advantages, the present invention will be particularly useful in mammography and thoracic radiography, imaging modalities that currently demonstrate high error rates of diagnostic sensitivity and specificity. However, it can also improve the accuracy of a broad range of radiographic imaging procedures used for detection of abnormal or diseased tissue.

In its general form, the present invention is a method for radiographic imaging of body tissue comprising:
  a) administering a cell membrane-permeable, radio-opaque imaging agent to a live organism;
  b) generating an X-ray beam;
  c) illuminating the tissue being examined with the X-ray beam; and
  d) acquiring a radiographic image of the tissue during illumination by the beam.

In another embodiment, a method includes:
  a) generating two or more X-ray beams with predetermined different energy spectra;
  b) illuminating the tissue with each of the X-ray beams;
  c) acquiring a radiographic image of the tissue during illumination by each of the X-ray beams; and
  d) performing a weighted combination of the acquired radiographic images to produce a single image.

The X-ray beams used in this embodiment may be quasi-monoenergetic or monoenergetic.

In one embodiment the method further includes displaying variable proportions of radiographic density contributed by the imaging agent, by soft tissue, and by bone to the displayed image.

In one embodiment of the method, the cell membrane-permeable, radio-opaque imaging agent selectively binds, either covalently or non-covalently, to a cellular target. The cellular target may be a cellular structure, such as an organelle, or a cellular molecule. The cellular target may be an enzyme, a non-enzyme protein, a coenzyme, a nucleic acid, or a lipid. In one embodiment of the invention, the cellular target is hexokinase.

In one embodiment of the invention, the imaging agent accumulates in malignant tissue at a different rate than in nonmalignant tissue. In another embodiment of the invention, the imaging agent accumulates in abnormal myocardial tissue at a different rate than in normal myocardial tissue.

One embodiment of the invention is a method for generating a functional image and an anatomical image of tissue in registration comprising:
  a) administering a radio-opaque imaging agent to a live organism;
  b) generating at least two X-ray beams with predetermined different energy spectra;
  c) illuminating the tissue being examined with each of the X-ray beams;
  d) acquiring a radiographic image of the tissue during illumination by each of the beams;
  e) generating the functional image from at least two of the acquired radiographic images.

In one embodiment, the radio-opaque imaging agent comprises a cell membrane-permeable composition having a general formula S-L-X, wherein:
  S is a binding moiety which selectively binds to a cellular molecule;
  X is a radio-opaque moiety; and
  L is a linking moiety which links the S moiety to the X moiety.

The invention, according to one embodiment, is based on the well-established principle that malignant tissue may be reliably distinguished from benign and normal tissue by its characteristically elevated rate of glucose metabolism.

Specifically, almost all types of malignant tissue metabolize glucose at a considerably higher rates than benign and normal tissue of the same body organ. It has also been established that malignant tissue contains elevated levels of a number of the enzymes active in glucose metabolism.

Hexokinase is an enzyme which is particularly overexpressed in malignant cells. Hexokinase catalyzes the first step in glucose metabolism, which is the phosphorylation of glucose to glucose-6-phosphate. Quantitative studies have consistently demonstrated elevated levels of hexokinase in malignant tissue, with the increased enzyme level approximately proportional to the increased tissue glucose metabolic rate. Hexokinase is therefore an appropriate target enzyme for detection and localization of malignant tissue.

Accordingly, one embodiment of the present invention utilizes a functional imaging agent which comprises a cell membrane-permeable, radio-opaque, high-affinity ligand for intracellular hexokinase. In this embodiment, a hexokinase substrate or inhibitor is linked to a non-radioactive, radio-opaque moiety in a manner that facilitates efficient passage of the imaging agent across the outer cell membrane (plasma membrane), direct entry into the cytosol, and selective binding with high affinity to the substrate binding site of intracellular hexokinase molecules. The cell membrane-permeable property of the imaging agent molecules insures their direct entry into the cytosol, and the exit of unbound imaging agent molecules across the cell membrane. Thus, imaging agent molecules that have bound to hexokinase are retained within the cell for at least a few hours. Unbound imaging agent molecules exit the cell at a relatively rapid rate, decreasing background radio-opacity and increasing contrast in the radiographic image. Because of the much higher concentration of hexokinase in malignant cells relative to benign and normal cells, the imaging agent accumulates in malignant tissue at an elevated level relative to benign and normal tissue.

In an example of a system and method according to the invention, a radiographic procedure is initiated by administering the imaging agent to a live patient. After the imaging agent accumulates throughout body tissue during a predetermined interval, the patient is appropriately positioned in relation to the X-ray source and image receptor, and radiographic images are acquired. Tissue that metabolizes glucose at a high rate, particularly malignant tissue, will have accumulated higher intracellular levels of the imaging agent than tissue that metabolizes glucose at a lower rate, such as benign and normal tissue. Because the imaging agent is radio-opaque, its differential accumulation causes corresponding differences in the absorption of the illuminating X-ray beam, which are manifested as differing levels of radiographic density on the radiograph.

In one embodiment of the invention, radiographic density contributed by the accumulated imaging agent is isolated from radiographic density contributed by soft tissue and bone. In this embodiment, the tissue being examined is sequentially transilluminated by X-ray beams with predetermined different mean energy spectra, and a separate radiographic image is acquired during transillumination by each beam. Using a predetermined weighting coefficient for each image, the image processing system performs a weighted combination of the acquired images to produce a single displayed image. The use of transilluminating X-ray beams with appropriate mean energy spectra together with appropriate weighting coefficients in the image processing procedure enables the cancellation on the displayed image of radiographic density contributed by soft tissue and bone. The remaining radiographic density present on the displayed image is contributed solely by differential intracellular accumulation of the radio-opaque imaging agent in malignant, benign, and normal tissue. Although this image of accumulated imaging agent is a functional image of tissue physiology, it is displayed with the high spatial resolution of a radiographic image.

The viewer may interactively vary the proportion of radiographic density contributed to the displayed image by accumulated imaging agent, by soft tissue, and by bone. A functional image of tissue combined with a variable degree of a superimposed anatomical image in registration may thereby be displayed. The combination of functional and anatomical information on a single image, or, if desired, on a series of images, facilitates the precise localization of malignant tissue in relation to nearby anatomical landmarks.

Advantages of the present invention include enhanced visibility of small areas of functionally abnormal tissue on the radiographic image, and improved differentiation of malignant tissue from benign tissue of increased radio-opacity. Examples of benign tissue of increased radio-opacity include cysts and fibroadenomas in the breast, and granulomas in the lung. Although cysts and fibroadenomas are the major sources of false positives in mammography, their rate of glucose metabolism is not elevated relative to that of normal tissue. The rate of glucose metabolism in granulomas, which are a major source of false positives in thoracic radiography, is likewise not elevated. Because the radio-opacity of cysts, fibroadenomas, and granulomas is not contributed by an increased accumulation of imaging agent, it is canceled by the imaging procedure of the present invention. The invention will therefore be particularly advantageous in eliminating these ubiquitous sources of false positives.

The invention may be used for imaging particular body organs such as the breast, lungs, liver and colon, in single or multiple images, or for imaging large areas of the body or the whole body in single or multiple images. In addition, it will be apparent to one skilled in the art that with the appropriate modifications to the imaging method and imaging agents, the present invention may be used in computed tomography and other radiographic modalities, as well as in standard radiographic imaging methods such as mammography and thoracic radiography.

The present invention is thus capable of generating images that combine the diagnostic accuracy provided by functional imaging of tissue physiology with the high anatomical detail and spatial resolution provided by radiography.

BRIEF DESCRIPTION OF THE DRAWINGS

FIGS. 3A and 3B show sectional and plan views respectively of the X-ray filter apparatus and its relationship to the X-ray source.

FIG. 8 is a flow chart of the multiple beam image acquisition and processing procedure.

DETAILED DESCRIPTION OF THE EMBODIMENTS

A. Radio-opaque Functional Imaging Agents

Figure 1:
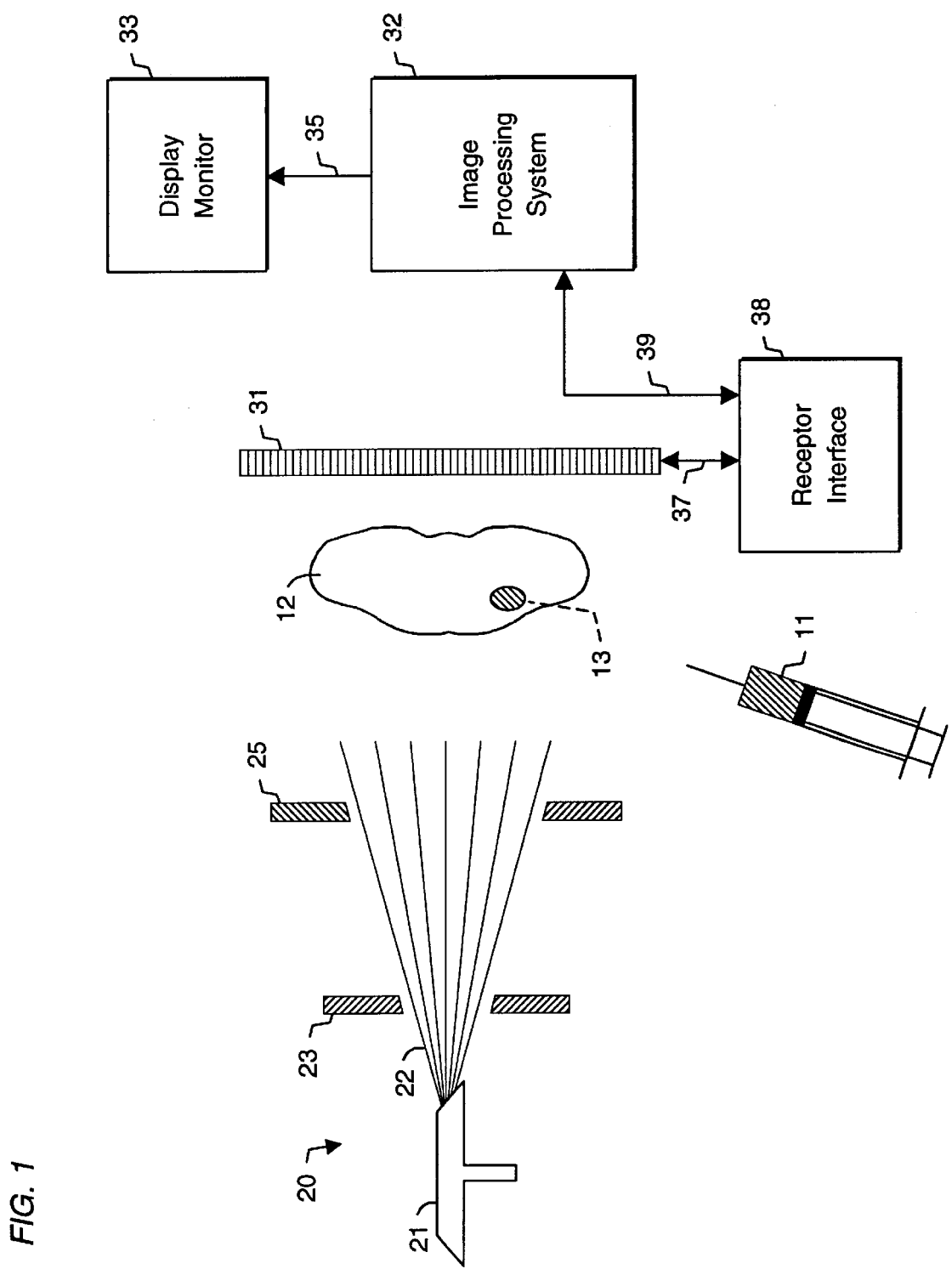
FIG. 1 is a block diagram of an embodiment of the imaging system using a single polyenergetic X-ray transilluminating beam.

In order to be optimally effective, a radiographic imaging agent should enhance the signal-to-noise ratio of abnormal or diseased tissue relative to normal tissue in the radiographic image. In the embodiments of the present invention, bidirectionally cell membrane-permeable radio-opaque imaging agents rapidly enter cells and selectively bind to cellular targets whose concentrations or activity is significantly different in abnormal or diseased tissue than in normal tissue. Accumulation levels of the imaging agents are therefore different in abnormal tissue than in normal tissue. The imaging agents also efficiently exit cells so that the intracellular concentration of unbound or unincorporated imaging agent decreases to a sufficiently low residual level to diminish background noise and enhance contrast on the radiographic image.

1. Imaging of Enzymes

One of the most prominent and characteristic abnormalities of malignant tissue is its elevated rate of glucose metabolism relative to normal tissue. It has long been known that this elevated metabolic rate is accompanied by a corresponding increase in the intracellular concentration and activity of the enzymes active in glucose metabolism.

In particular, studies have repeatedly demonstrated that the considerable elevation of glucose metabolic rate in malignant tissue is accompanied by elevated levels of hexokinase activity. Hexokinase catalyzes the first step in glucose metabolism, which is the phosphorylation of glucose to glucose-6-phosphate. Malignant cells markedly overexpress hexokinase relative to benign and normal cells from the same organ [Weber G: Garn Monogr. Cancer Res. 13: 47–77 (1972); Weinhouse S: Cancer Res. 32: 2007–2016]. A portion of intracellular hexokinase is located in the cytosol in soluble form, and another portion is located in the cytosol and attached to the outer mitochondrial membrane [Arora K K, Pedersen P L: J. Biol. Chem. 263: 17422–17428 (1988)]. The hexokinase activity of normal, benign and malignant tissue is roughly proportional to their respective rates of glucose metabolism. Kinetic analysis of the k compartments in PET glucose imaging studies indicates that the increase in glucose metabolic rate in malignant tissue can largely be accounted for by increased activity of hexokinase in the $k_3$ (phosphorylation) compartment. The detection and quantitation of hexokinase is thus a particularly useful method for identification of malignant tissue.

Accordingly, one embodiment of the radio-opaque functional imaging agent of the present invention is a cell membrane-permeable, high-affinity ligand for intracellular hexokinase. In this embodiment, a hexokinase substrate or inhibitor is linked to a non-radioactive, radio-opaque moiety in a manner that permits efficient diffusion of the imaging agent across the cell membrane into the cytosol and attachment with high affinity to the substrate binding site of intracellular hexokinase molecules. In one embodiment, the molecule may comprise an amino sugar, in pyranose or furanose form, attached by means of a covalent linkage arm to a moiety containing one or more atoms of a radio-opaque element, which may be iodine.

The protein structures of yeast and human hexokinases have been determined using both X-ray crystallography and the known amino acid sequences of the enzymes [Willson M et al.: J Enz Inhib. 12: 101–121 (1997); St. Charles R et al.: Diabetes 43: 784–791 (1994); Aleshin A E et al.: Structure 6: 39–50 (1998)], and the relative activity of many of their substrates and inhibitors has been experimentally determined [Sols A, Crane R K: J. Biol. Chem. 210: 581–595 (1954); Maley F, Lardy H A: J Biol Chem. 214: 765–773 (1955); Coats E A et al.: J Enz Inhib. 6: 271–282 (1993)] . These published results, in combination with original molecular modeling studies, provide data necessary for the design of cell-permeable, radio-opaque, high affinity ligands for hexokinase described in the present invention.

The structural interactions of hexokinase with its substrates and inhibitors have been well characterized. Both pyranose and furanose ring structures can bind to the substrate binding site of the enzyme with high affinity. Based on published data and the present modeling studies, the optimal strategy for attachment of moieties to the sugar resulting in the least steric hindrance of the substrate binding site of the enzyme is substitution of the hydroxy group at the C-2 position of the pyranose or furanose ring. In addition, these studies suggest that a linkage arm of appropriate design inserted between the enzyme binding moiety and the radio-opacifying moiety can significantly improve the affinity of the imaging agent for hexokinase. The improvement in affinity for the enzyme is provided by two functions of the linkage arm. One function is to minimize steric hindrance of the substrate binding site by the radio-opaque moiety of the imaging agent. The second function is to enhance binding of the imaging agent molecule to the enzyme through beneficial interactions, including hydrogen bonds and van der Waals contacts, with amino acid residues in the vicinity of the binding site.

In the present studies, conformational searches and QSAR analysis were used to determine optimal characteristics of the linkage arm and to identify energetically feasible conformers. The most important characteristics of the linkage arm were found to be its length, its bulk, and its interaction with amino acid residues in the vicinity of the substrate binding cavity of the enzyme. It has been determined that to avoid unwanted steric interactions between the radio-opaque moiety and the binding site of the enzyme, the chain length of the linkage arm separating the pyranose or furanose ring from the radio-opaque moiety, as measured from the C-2 atom of the ring to the proximal atom of the radio-opaque moiety, should be a minimum of approximately 8 A. Shorter chain lengths may allow unwanted interactions between the radio-opaque moiety and residues local to the substrate binding site. Longer chain lengths may produce unwanted non-specific interactions with other intracellular components, although longer chain lengths may be used with the present invention.

In addition, substituents may be inserted into the linkage arm to further improve the binding affinity of the imaging agent for the enzyme. A particularly effective linkage arm is comprised of a benzoic acid moiety containing a polar substituent, such as a nitro- or amino- group, in the ortho or meta position. However, substituent characteristics should be carefully controlled. For example, substituent bulk above a certain size may result in steric hindrance and a sharp decrease in binding affinity.

In addition to the requirement of high affinity for hexokinase, the imaging agent of one embodiment should readily permeate the cell membrane and enter the cytosol in order to bind intracellular enzyme molecules. Further, imaging agent molecules which have not attached to enzyme molecules should efficiently exit the cell to effectively reduce background radio-opacity. Glucose is normally transported bidirectionally across the cell membrane by means of one or more of the GLUT transport proteins. Substituents in, or moieties linked to, the basic pyranose or furanose ring can inhibit transport by these proteins. Design of the imaging agent so that it is lipophilic insures its efficient bi-directional diffusion across the cell membrane, without the necessity for facilitated transport by the GLUT proteins.

In these studies, lipophilicity of imaging agents was characterized by computed logP. Lipophilicity is defined as the partitioning of a compound between an aqueous and a nonaqueous phase, with the nonaqueous phase usually chosen to be noctanol. LogP is the log of the partition coefficient of a compound between the two phases, and is a standard measure of lipophilicity in biological systems. For a wide range of small non-ionic molecules, strong correlations have been experimentally verified between logP and the distribution of the molecule between the aqueous medium and the cell membrane [Hansch et al.: J. Pharm Sci. 61: 1–19 (1972)]. Using appropriate models, computed values of logP can correlate closely with measured values [Ghose A K et al.: J. Comp. Chem. 9: 80–90 (1988); Rekker R F, Mannhold R: Calculation of Drug Lipophilicity, VCH, Weinheim, (1992); Meylan W M, Howard P H: J. Pharm. Sci. 84: 83–92 (1995)]. Commonly used radiographic contrast agents generally have molecular weights of below 1000 daltons. For molecules of this size, the logP should be above 0.0 and should preferably be in the range of approximately 0.0 to approximately 6.0 to enable optimal passive diffusion across the cell membrane. Table 1 shows experimental logP values and molecular weights of some commonly used non-ionic radiographic contrast agents [Hansch et al: Exploring QSAR, Amer. Chem Soc., Washington DC (1995)]. The table also shows computed logP values and molecular weights of glucose and of representative iodo-substituted hexose imaging agents disclosed by Ledley and Gersten (U.S. Pat. No. 4,716,225). The computed logP values and molecular weights of Examples 1–3 of the present invention are also shown.

TABLE 1

| Compound | logP | MW | U.S. Pat. No. |
|---|---|---|---|
| Iohexol | −3.05 | 821.14 | 4,250,113 |
| Iopromide | −2.05 | 791.12 | 4,364,921 |
| Metrizamide | −1.86 | 789.10 | 3,701,771 |
| Glucose | −2.89 | 180.16 | — |
| 6-Iodo-galactose | −1.73 | 290.06 | 4,716,225 |
| 2-Iodo-galactose | −2.08 | 290.06 | 4,716,225 |
| Example 1 | +4.64 | 752.08 | present |
| Example 2 | +5.31 | 779.13 | present |
| Example 3 | +2.65 | 866.19 | present |

The molecular weights of the compounds in Table 1 are all below 1000 daltons. The logP values of the first three contrast agents are below 0.0, and are consistent with their demonstrated hydrophilicity and inability to permeate cell membranes. The logP values of all iodo-substituted hexose compounds disclosed by Ledley and Gersten, two representative examples of which are listed in Table 1, are also below 0.0. In contrast, Examples 1–3 of the present invention have logP values above 0.0, and their relatively high lipophilicity enhances their passive diffusion across the cell membrane and entry into the cytosol.

The radio-opaque moiety of the imaging agent contains one or more atoms of an element, which may be iodine, which exhibits suitable radio-opacity in the photon energy spectrum emitted by a typical diagnostic X-ray source operated at approximately 50 keV to approximately 80 keV. Although iodine is the most common radio-opaque element used for enhancement of radiographic contrast, other selected elements may be used in the radio-opaque moiety in alternate embodiments of the imaging agent. The suitability of an element for use in the radio-opaque moiety will depend on the photon energy of the element's K-absorption edge, a property explained in detail in section E. It will also be appreciated that X-ray sources of lower or higher energy may also be used with the invention. Radio-opaque elements with higher K-absorption edges may generally be used with X-ray beams of higher photon energy, and elements with lower K-absorption edges may generally be used with X-ray beams of lower photon energy.

The general form of one embodiment of the radio-opaque imaging agent is

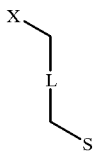

wherein:
the S moiety is a pyranose or a furanose;
the X moiety is an unsubstituted or substituted $C_1$–$C_8$ alkyl, alkoxy, alkylthio, alkenyl, alkylaryl, alkylamino, alkylamido, amido, or arylamido, in which at least one atom is substituted by a radio-opacifying atom of an element with an atomic number of between approximately Z=35 to approximately Z=74; and
the L moiety is an unsubstituted or substituted $C_1$–$C_8$ alkyl, alkoxy, alkylthio, alkenyl, alkylayl, alkylamino, alkylamido, amido, or arylamido, bonded to the S moiety and to the X moiety.

Functionalized groups, including hydrophilic groups containing one or more hydroxyls or carbamoyls, may be also optionally be substituted at one or more positions of the X moiety to shield the radio-opacifying atom or atoms from causing chemotoxic responses in vivo.

In one embodiment, the S moiety is a pyranose or furanose that attaches to the binding site of an intracellular enzyme; the X moiety is radio-opaque in the portion of the energy spectrum typically used in diagnostic radiographic imaging; and the L moiety is bonded to the S moiety and to the X moiety. The L moiety positions the X moiety at a sufficient distance from the pyranose or furanose ring to prevent steric hindrance of the binding site, and enhances affinity of the molecule for the enzyme through hydrogen bonds and Van der Waals interactions with residues in the vicinity of the substrate binding site, and amide-amide interactions with the protein backbone.

It will be understood that the use of the above terms in the case of residues that can be substituted or unsubstituted will include the reasonably substituted forms of such residues as well as their unsubstituted forms. Reasonable substitutions which will produce useful compounds will be evident to one skilled in the art and will include such substituents, without limitation, as amino, nitro, hydroxy, carboxy, carbamoyl, to name just a few.

Methods of syntheses for Examples 1–3 employ reactions commonly used in synthetic chemistry and will be well known to those of ordinary skill in the art.

EXAMPLE 1

2-Amino4(2',4',6'-triiodophenyl)-benzoyl-D-glucosamine (11)

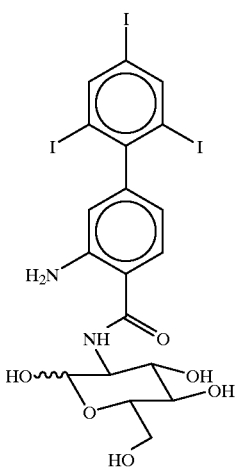

4-iodotoluene is reacted with picryl chloride in the presence of copper bronze at 215° C. to yield 2',4',6'-trinitro-4-methylbiphenyl (1).

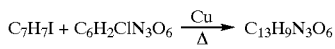

2',4',6'-trinitro-4-methylbiphenyl (1) is reacted with stannous chloride and hydrochloric acid to yield 2',4',6'-triamino-4-methylbiphenyl (2).

2',4',6'-triamino-4-methylbiphenyl (2) is reacted with sodium nitrite and hydrochloric acid to convert the amino groups to diazonium groups. The diazonium groups react with potassium iodide to yield 2',4',6'-triiodo-4-methylbiphenyl (3).

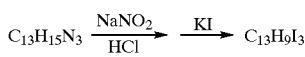

Aromatic nitration of 2',4',6'-triiodo-4-methylbiphenyl (3) is performed with nitric acid and sulfuric acid to yield a mixture of 2',4',6'-triiodo-2-nitro-4methylbiphenyl (4) and 2',4',6'-triiodo-3-nitro4-methylbiphenyl (5). The products are separated using column chromatography.

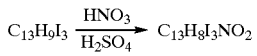

The methyl group of 2',4',6'-triiodo-3-nitro-4-methylbiphenyl (5) is oxidized by potassium permanganate to yield 2',4',6'-triiodo-3-nitrobiphenyl-4-carboxylic acid (6).

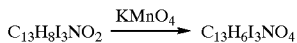

2',4',6'-triiodo-3-nitrobiphenyl-4-carboxylic acid (6) is reacted with thionyl chloride to yield 2',4',6'-triiodo-3-nitrobiphenyl-4-carbonyl chloride (7).

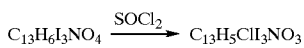

The hydroxyl groups of D-Glucosamine (8) are protected by reaction with acetic anhydride in the presence of pyridine to yield 1,3,4,6-tetra-O-acetyl-D-glucosamine (9).

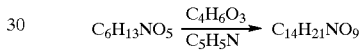

1,3,4,6-tetra-O-acetyl-D-glucosamine (9) is reacted with 2',4',6'-triiodo-3-nitrobiphenyl-4-carbonyl chloride (7) to yield 2-nitro-4-(2',4',6'-triiodophenyl)-benzoyl-1,3,4,6-tetra-O-acetyl-D-glucosamine (10).

2-nitro-4-(2',4',6'-triiodophenyl)-benzoyl-1,3,4,6-tetra-O-acetyl-D-glucosamine (10) is treat with stannous chloride in the presence of hydrochloric acid to yield 2-amino-4-(2',4',6'-triiodophenyl)-benzoyl-D-glucosamine (11).

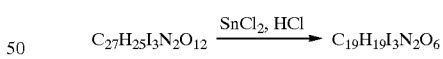

In Example 1, 2-Deoxy-D-glucose is 2-hydroxy-substituted with a o-aminobenzamide linkage arm, which links the pyranose to a triiodophenyl moiety. The pyranose ring binds to the substrate binding site of hexokinase. The o-aminobenzamide linkage arm enhances the binding of the pyranose to the binding site, and also spaces the radio-opaque tri-iodophenyl moiety a sufficient distance from the pyranose to prevent steric hindrance of the binding site. The triiodophenyl configuration provides strong carbon-iodine bonds and thereby insures resistance to deiodination in vivo. Lipophilicity enhances bidirectional diffusion of the molecule across the cell membrane, and is contributed by both the linkage arm and the radio-opaque moiety. The computed logP of Example 1 is 4.64.

EXAMPLE 2

2-Amino-4-(3'-ethyl-2',4',6'-triiodophenyl)-benzoyl-D-glucosamine (16)

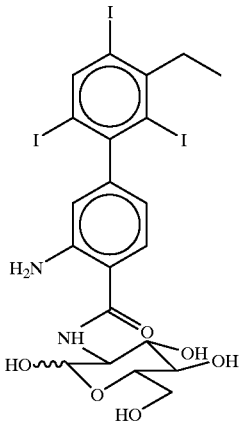

Freidel-Crafts acylation is performed on 2',4',6'-triiodo-3-nitrobiphenyl-4-carboxylic acid (6) in the presence of AlCl$_3$ and CH$_3$COCl to yield 2',4',6'-triiodo-3'-acetyl-3-nitrobiphenyl-4-carboxylic acid (12).

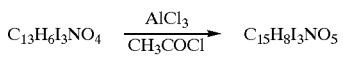

2',4',6'-triiodo-3'-acetyl-3-nitrobiphenyl-4-carboxylic acid (12) is then reacted with a zinc mercury amalgam and hydrochloric acid and heated to yield 2',4',6'-triiodo-3'-ethyl-3-nitrobiphenyl-4-carboxylic acid (13).

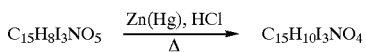

2',4',6'-triiodo-3'-ethyl-3-nitrobiphenyl-4-carboxylic acid (13) is reacted with thionyl chloride to yield 2',4',6'-triiodo-3'-ethyl-3-nitrobiphenyl-4-carbonyl chloride (14).

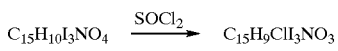

1,3,4,6-tetra-O-acetyl-D-glucosamine (9) is reacted with 2', 4', 6'-triiodo-3'-ethyl-3-nitrobiphenyl-4-carbonyl chloride (14) to yield 2-nitro-4-(3'-ethyl-2', 4', 6'-triiodophenyl)-benzoyl-1,3,4,6-tetra-O-acetyl-D-glucosamine (15).

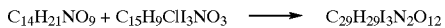

2-nitro-4-(3'-ethyl-2',4',6'-triiodophenyl)-benzoyl-1,3,4,6-tetra-O-acetyl-D-glucosamine (15) is treated with stannous chloride and hydrochloric acid to yield 2-amino-4-(3'-ethyl-2',4',6'-triiodophenyl)-benzoyl-D-glucosamine (16).

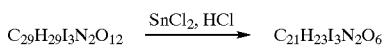

Example 2 is similar in general structure to Example 1, with the additional presence of a short alkyl chain attached to the radio-opaque tri-iodophenyl moiety at the C-3' position to further increase lipophilicity of the molecule and enhance cell membrane permeability. The computed logP of Example 2 is 5.31.

EXAMPLE 3

2-Amino-4-[3',5'-bis(N-methylcarboxamide)-2',4',6'-triiodophenyl]-benzoyl-D-glucosamine (24)

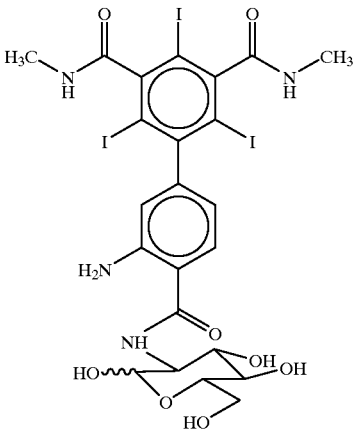

Freidel-Crafts acylation is performed on 2',4',6'-triiodo-3'-ethyl-3-nitrobiphenyl-4-carboxylic acid (13) in the presence of AlCl$_3$ and CH$_3$COCl to yield 2',4',6'-triiodo-3'-ethyl-5'-acetyl-3-nitrobiphenyl-4-carboxylic acid (17). 2',4',6'-triiodo-3'-ethyl-5'-acetyl-3-nitrobiphenyl-4-carboxylic acid (17) is then reacted with a zinc mercury amalgam and hydrochloric acid and heated to yield 2',4',6'-triiodo-3',5'-bis(ethyl)-3-nitrobiphenyl-4-carboxylic acid (18)

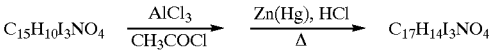

2',4',6'-triiodo-3',5'-bis(ethyl)-3-nitrobiphenyl-4-carboxylic acid (18) is reacted with thionyl chloride to yield 2',4',6'-triiodo-3',5'-bis(ethyl)-3-nitrobiphenyl-4-carbonyl chloride (19).

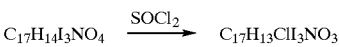

1,3,4,6-tetra-O-acetyl-D-glucosamine (9) is reacted with 2',4',6'-triiodo-3',5'-bis(ethyl-3-nitrobiphenyl-4-carbonyl chloride (19) to yield 2-nitro-4-[3',5'-bis(ethyl)-2',4',6'-triiodophenyl]benzoyl-1,3,4,6-tetra-O-acetyl-D-glucosamine (20).

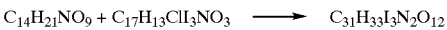

2-nitro-4-[3',5'-bis(ethyl)-2',4',6'-triiodophenyl]-benzoyl-1,3,4,6-tetra-O-acetyl-D-glucosamine (20) is oxidized with potassium permanganate to yield 2-nitro-4-[3',5'-bis(carboxylic acid)-2',4',6'-triiodophenyl]-benzoyl-1,3,4,6-tetra-O-acetyl-D-glucosamine (21).

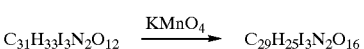

2-nitro-4-[3',5'-bis(carboxylic acid)-2',4',6'-triiodophenyl]-benzoyl-1,3,4,6-tetra-O-acetyl-D-glucosamine (21) is reacted with ethanol and weak hydrochloric acid and heated to yield 2-nitro-4-[3',5'-bis(ethoxycarbonyl)-2',4',6'-triiodophenyl]-benzoyl-1,3,4,6-tetra-O-acetyl-D-glucosamine (22).

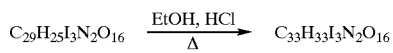

2-nitro-4-[3',5'-bis(ethoxycarbonyl)-2',4',6'-triiodophenyl]-benzoyl-1,3,4,6-tetra-O-acetyl-D-glucosamine (22) is reacted with methylamine to yield 2-nitro-4-[3',5'-bis(N-methylcarboxamide)-2',4',6'-triiodophenyl]-benzoyl-1,3,4,6-tetra-O-acetyl-D-glucosamine (23).

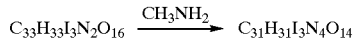

2-nitro-4-[3',5'-bis(N-methylcarboxamide)-2',4',6'-triiodophenyl]-benzoyl-1,3,4,6-tetra-O-acetyl-D-glucosamine (23) is treated with stannous chloride and hydrochloric acid to yield 2-amino-4-[3',5'-bis(N-methylcarboxamide)-2',4',6'-triiodophenyl]-benzoyl-D-glucosamine (24).

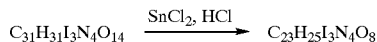

Example 3 is similar in overall structure to Example 1, with the addition of hydrophilic groups added at positions C-3' and C-5' of the radio-opaque aromatic ring to help shield the iodine atoms from causing chemotoxic effects in vivo. The computed logP of Example 3 is 2.65.

Other functionalized groups, including hydrophilic groups containing one or more hydroxyls or carbamoyls, may be also optionally be substituted at the 3' and 5' positions to help shield the iodine atoms from causing chemotoxic responses in vivo.

The examples shown above are directed toward the radiographic imaging of the elevated glucose metabolic rate of malignant tissue. However, it will be apparent to one skilled in the art that imaging agents for other target enzymes may be synthesized by combining a substrate or inhibitor of the enzyme with a radio-opaque moiety in a manner that permits diffusion of the imaging agent across cell membranes and selective binding to the target enzyme. Imaging agents of this general form may be used for the radiographic detection of a wide variety of normal and abnormal enzymes expressed at varying levels in normal and abnormal body tissue.

2. Imaging of Nucleic Acids

In situ hybridization is a technique for detection of specific DNA or RNA sequences within cells. The technique may be implemented with an oligonucleotide consisting of a single stranded, predefined sequence of nucleotides which is complementary to a selected nucleotide sequence in an intracellular target DNA or RNA molecule. Such oligonudeotides are generally obtained by chemical synthesis or by enzymatic polymerization.

A number of methods have been described for in situ hybridization of labeled oligonucleotides in living cells. Singer et al. (U.S. Pat. No. 5,728,527) disclosed a method of detecting labeled hybridized nucleotide probes in situ. In the disclosed method, oligonucleotides were labeled with a fluorophore or with a radioactive isotope. Cells were incubated in the presence of labeled oligonucleotide for a predetermined amount of time to allow the oligonucleotide to enter cells and to hybridize with intracellular target molecules. The cells were then washed to remove unhybridized oligonucleotides. The intracellular level of remaining hybridized oligonucleotides was then determined by measurement of fluorescence or radioactivity.

The technique has been extended to imaging of nucleotide sequences in vivo. Small tumors have been imaged with $^{111}$In-labeled oligonucleotides using a gamma camera in a mouse mammary tumor model [Dewanjee M K et al.: J. Nuc. Med. 35: 1054–1063 (1994). In vivo imaging of oligonucleotides using positron emission tomography has also been reported [Tavitian et al.: Nature Medicine 4: 467–471 (1998)]. In the PET study the positron emitter $^{18}$F was used to label oligonucleotides at the 3-terminus of the oligomer.

Oligonucleotides have typically been synthesized with the native phosphodiester internucleotide linkages. It has been shown that phosphodiester-bonded oligonucleotides enter cells by means of receptor-mediated endocytosis [Loke S L et al.: Proc. Natl. Acad. Sci. USA 86: 3474–3478 (1989)]. In this mode of cellular entry, oligonucleotides molecules attach to receptors on the cell surface and are internalized into the cell through pinching off of the cell membrane to form intracellular vesicles. Although the oligonucleotides are physically localized within the cell, they are separated from the cytosol by the membrane surrounding the vesicles. They therefore do not have direct access to the cytosol, and because of this presumably interact with intracellular RNA and DNA molecules at a relatively inefficient rate.

Alterations have also been made to the phosphodiester backbone of oligonucleotides to decrease their negative charge and increase their lipophilicity. [Bischofberger et al: U.S. Pat. No. 5,763,208; Matteucci M: Ciba Found. Symp. 209: 5–18 (1997); Cook et al.: U.S. Pat. No. 5,610,289]. Alterations have also been made to oligonucleotides to increase their resistance to nucleases [Agrawal S, Zhang R: Ciba Found. Symp. 209: 60–75 (1997)].

The requirements for a functional radiographic imaging agent for imaging of target DNA and RNA sequences in vivo should include the use of an oligonucleotide sequence complementary to a target intracellular nucleic acid sequence. The imaging agent should be able to bidirectionally permeate the cell membrane and enter the cell with high efficiency. Cell membrane-permeability should increase the efficiency with which the oligonucleotides can hybridize with intracellular target DNA and RNA molecules. The imaging agent should be radio-opaque in the region of the photon energy spectrum used in diagnostic radiographic imaging. The imaging agent should also be resistant to degradation by nucleases.

Accordingly, one embodiment of the functional imaging agent of the present invention is a cell membrane-permeable radio-opaque oligonucleotide capable of binding to intracellular target DNA or RNA molecules. One embodiment of the imaging agent may use an oligonucleotide with a predetermined nucleotide sequence capable of hybridizing to a complementary nucleotide sequence present in abnormal or diseased body tissue. In one embodiment, the selected oligonucleotide may have a sequence complementary to an RNA or DNA target sequence expressed only in malignant tissue, only in normal tissue, or expressed at a different level in malignant tissue than in nonmalignant tissue. The radio-opacity of the imaging agent and its accumulation in cells containing the targeted nucleic acid sequence thus permits the detection of a predetermined nucleic acid sequence in vivo in a radiographic imaging procedure using the imaging methods of the present invention.

In one embodiment, a radio-opaque moiety is attached via a covalent linkage arm to the oligonucleotide at its 5'-terminus. In another embodiment, the radio-opaque moiety and linkage arm may be attached to the oligonucleotide at its 3'-terminus. The linkage arm is made sufficiently long so that the radio-opaque moiety does not impede hybridization of the oligonucleotide with the target molecule. In molecular modeling studies it was determined that a linkage arm of approximately 5–6 carbons, or approximately 5–6 Å in length, places the radio-opaque moiety a sufficient distance from a 5'-terminal nucleotide to prevent interference of hybridization of the oligonucleotide with a target sequence. A long linkage arm may also increase lipophilicity of the imaging agent and enhance its entry into cells. In one embodiment, an aromatic ring bonded to iodine atoms may be used as the radio-opaque moiety to provide strong carbon-iodine bonds and consequent resistance to deiodination in vivo.

In one embodiment, the imaging agent is capable of entering and exiting the cell via passive diffusion across the cell membrane. To enhance passive diffusion, the imaging agent molecule may be made lipophilic by either or both of two modifications of the native oligonucleotide. First, negatively charged phosphodiester linkages in the oligonucleotide backbone may be partially or completely replaced by formacetal, aminohydroxy, or other nonionic internucleotide linkages. Second, the oligonucleotide may be made additionally lipophilic. Methods for increasing lipophilicity include addition of hydrophobic moieties, such as an upper alkyl chain, to the 3'- or 5'-terminus of the oligomer. Lipophilic additions may also be made to one or more of the nucleotides with substitutions in purines, pyrimidines, or sugars.

The general form of one embodiment of the radio-opaque imaging agent is

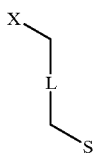

wherein:

the S moiety is an oligonucleotide in which the nucleotide sequence comprises at least two residues;

the X moiety is an unsubstituted or substituted $C_1$–$C_8$ alkyl, alkoxy, alkylthio, alkenyl, alkylaryl, alkylamino, alkylamido, amido, or arylamido, in which at least one atom is substituted by a radio-opacifying atom of an element with an atomic number of approximately Z=35 to approximately Z=74; and the L moiety is an unsubstituted or substituted $C_1$–$C_8$ alkyl, alkoxy, alkylthio, alkenyl, alkylaryl, alkylamino, alkylamido, amido, or arylamido, bonded to the S moiety and to the X moiety.

In one embodiment the internucleotide linkages of the S moiety may comprise nonionic linkages, including but not limited to formacetal or aminohydroxy linkages, between the C-5' position of the nucleotide sugar and the C-3' position of the adjacent nucleotide sugar.

In one embodiment, one or more lipophilic groups, including but not limited to $C_6$–$C_{30}$ alkyl chains, may be attached at one or more locations on the S moiety, the X moiety, and the L moiety.

Functionalized groups, including hydrophilic groups containing one or more hydroxyls or carbamoyls, may be also optionally be substituted at one or more positions of the X moiety to shield the radio-opacifying atom or atoms from causing chemotoxic responses in vivo.

EXAMPLE 4

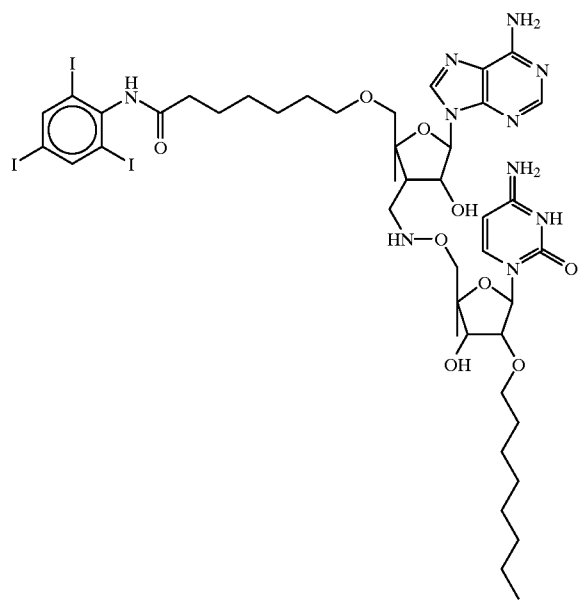

In Example 4, a oligonucleotide dimer is substituted with an aminohydroxy internucleotide linkage for the native phosphodiester linkage and a $C_8$ alkyl chain is substituted at a 2'-sugar position of the oligomer. The oligomer is linked to a radio-opaque moiety by means of a $C_6$ alkylamido linkage arm. One end of the linkage arm is bonded to the 5'-terminus of the oligomer, and the other end is bonded to a triiodophenyl moiety. The triiodophenyl configuration of the radio-opaque moiety provides strong carbon-iodine bonds and resistance to deiodination in vivo.

Methods for synthesis of the embodiments described above will be well known to one of ordinary skill in the art. Specifically, methods for synthesis of oligonucleotides and for conjugation of a wide variety of groups to the 3'-terminus and the 5'-terminus are well known [Crooke et al., eds: Antisense Research and Applications, CRC Press, Boca Raton Fla. (1993)]. Methods for synthesis of non-ionic internucleotide backbones have been described [Bischofberger et al.: U.S. Pat. No. 5,763,208; Cook et al.: U.S. Pat. No. 5,610,289]. Synthesis of oligonucleotides containing modifications to the 2'-sugar positions has also been described. [Keller T H, Haner R: Nucl. Acids Res. 21: 4499–4505 (1993); Buhr et al., U.S. Pat. No. 5,466,786].

Although the embodiments described in the present invention are directed toward the detection of nucleic acids expressed in malignant tissue, it will be evident to one skilled in the art that the method may be adapted for the radiographic detection of nucleic acids present in abnormal tissue in a wide variety of diseases. The method may additionally be also used to detect the presence of any nucleic acid sequence present in tissue, whether the nucleic acid originates in the tissue itself or in foreign organisms such as bacteria or viruses present in the tissue. In each case the specific oligonucleotide sequence to be used will be determined by the complementary DNA or RNA sequence to be detected.

3. Imaging of Fatty Acids

Many common cardiac disorders result in disturbances of myocardial metabolism. Because the oxidation of long-chain fatty acids is the major energy pathway in myocardial tissue, imaging of fatty acid metabolism has become an important modality for diagnosis of disorders of myocardial tissue. Abnormal rates of cellular uptake, synthesis, and breakdown of long-chain fatty acids have been demonstrated in a range of cardiac abnormalities, including coronary artery disease, myocardial infarction, cardiomyopathies, and ischemic tissue. [Railton R et al.: Euro. J. Nucl. Med 13: 63–67 (1987); Van Eenige M J et al.: Eur Heart J. 11: 258–268 (1990)].

Fatty acids generally enter cells through passive diffusion [Trigatti B L et al.: Biochem. J. 313: 487–394 (1996); Kamp F et al.: Biochemistry 34: 11928–11937 (1995); Kamp F et al.: Biochemistry 32: 11074–11086 (1993)]. After cellular entry, a portion of fatty acids undergo β-oxidation. The first step in this metabolic pathway is activation of the fatty acid molecule by combination with coenzyme A (CoASH) in the presence of ATP to form acyl CoASH. This step is catalyzed by fatty acyl coenzyme A synthetase, and occurs in the endoplasmic reticulum and the outer mitochondrial membrane. The remaining portion of fatty acids which enter myocardial cells is primarily incorporated into cellular triglycerides and membrane phospholipids. It has been demonstrated that the rates of β-oxidation and esterification of fatty acids are reduced in a wide range of myocardial disorders. Imaging of intracellular fatty acid metabolism using radiolabeled fatty acids in conjunction with SPECT and PET imaging devices has been shown to be an accurate diagnostic indicator of myocardial abnormality.

Accordingly, one embodiment of the present invention is a non-radioactive, radio-opaque imaging agent comprised of a long-chain fatty acid attached to a radio-opaque moiety. After administration to a patient, the imaging agent rapidly enters myocardial cells via passive diffusion across the cell membrane. The tissue distribution of this imaging agent may be imaged using the single and multiple beam imaging methods described in the present invention.

EXAMPLE 5

15-(p-Iodophenyl)pentadecanoic acid

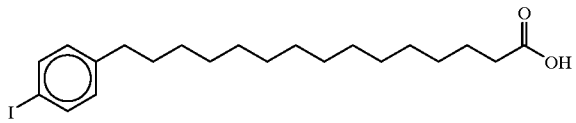

Example 5 shows an imaging agent comprising an co-iodophenyl-substituted straight-chain fatty acid, 15-(p-Iodophenyl)pentadecanoic acid (IPPA). The radioactive form of this molecule, and its synthesis, has been described. [Machulla H J et al.: J. Nucl. Med. 19: 298–302 (1978)]. After entry into myocardial cells, a fraction of IPPA is quickly β-oxidized. Another fraction of the IPPA is incorporated into cardiac triglycerides and membrane phospholipids [Chien et al.: Am. J. Physiol. 245: H693–H697 (1983)]. In the embodiment of the current invention, the imaging agent is non-radioactive, which allows its use in cardiac imaging procedures using standard radiographic imaging devices. The need for synthesis of radiopharmaceuticals and gamma camera imaging is thereby eliminated. As in previous examples, the iodophenyl configuration provides a strong carbon-iodine bond and consequent resistance to deiodination in vivo. Example 5 is lipophilic, and enters and exits the cell via passive diffusion across the cell membrane. The computed logP of Example 5 is 8.09.

It will be apparent to one of ordinary skill in the art that variants of the non-radioactive, radio-opaque fatty acids described here may be readily synthesized. In particular, these variants include the replacement of straight chain fatty acids with methyl-branched and p-phenylene-bridged fatty acids to increase tissue retention time [Torikuza K et al.: Jpn. J. Nucl. Med. 28: 681–690 (1991); Eisenhut M et al.: Int. J. Rad. Appl. Instrum. 39: 639–649 (1988)].

4. Imaging of Other Targets

The embodiments of the radio-opaque functional imaging agent shown above are designed for the detection of enzymes, nucleic acids, and fatty acids. In addition, some of the embodiments of the present invention may be primarily used for the diagnosis of malignant tissue. However, radiographic imaging agents with a wide variety of diagnostic functions may be developed using the design principles disclosed in the present invention. For example, cell membrane-permeable imaging agents may be synthesized which selectively bind to carbohydrates, lipids, other intracellular molecules, or cell structures or organelles. The system and method may thus be modified to provide radiographic detection of other cellular targets of diagnostic importance.

In the examples shown in the present invention, the radio-opaque element in the imaging agent is iodine. However, it will be apparent to one skilled in the art that other elements exhibiting sufficient radio-opacity in the photon energy spectrum used in radiography, and possessing acceptable physiological and toxicological characteristics, may be incorporated into the radio-opaque moiety of the imaging agent. In each application, the choice of the element will depend on the goal of the diagnostic imaging procedure, the necessary physical and chemical characteristics of the imaging agent, and the energy spectrum of the transilluminating X-ray beam.

B. Single Beam Imaging System

FIG. 1 is a block diagram of a first embodiment of the imaging system, as used in an imaging procedure performed with a single, continuous spectrum, polyenergetic X-ray transilluminating beam. A cell membrane-permeable radio-opaque imaging agent 11 is administered to a patient. During a predetermined time interval the imaging agent accumulates in the patient's normal body tissue 12, and at a different rate in any abnormal tissue 13 that may be present.

An X-ray illumination source 20, which may include an ordinary X-ray tube with a tungsten anode 21, produces a continuous spectrum polyenergetic beam 22. A first collimator 23 directs the beam. A second collimator 25 further directs the beam. An X-ray image receptor 31, which may be radiographic film, a film/intensifying screen combination, a stimulable phosphor storage plate, a fluoroscopic image intensifier, an amorphous silicon sensor array, a CCD/scintillator combination, or another type of X-ray sensitive receptor, acquires a radiographic image of body tissue during transillumination by beam 22. A receptor interface 38 acquires 37 the received image in a manner dependent on the type of receptor 31. If the receptor is film or a film/intensifying screen combination, the film may be processed, and then viewed directly or scanned and digitized by the interface. If the receptor is a stimulable phosphor storage plate, the plate is read out and digitized by the interface. If the receptor is a fluoroscopic image intensifier or CCD/scintillator combination, the analog output of the detector is digitized by the interface. If the receptor is an amorphous silicon sensor array, the analog output is digitized by the interface or a digital output, if available, may be used directly. Receptor interface 38 transfers the digitized image data to an image processing system 32, which may be a computer, over signal lines 39.

Figure 1A:
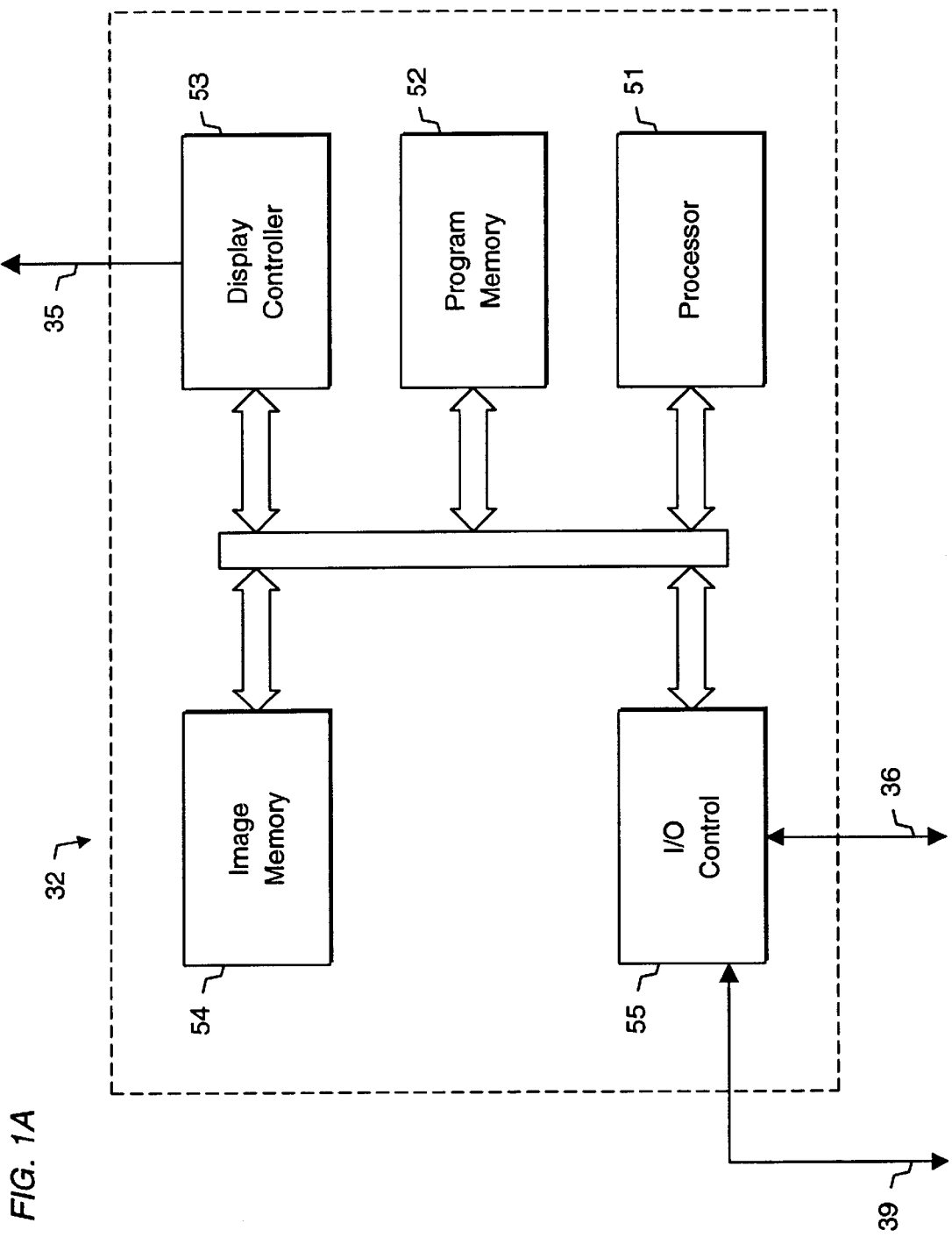
FIG. 1A is a block diagram of the image processing system.
Figure 2:
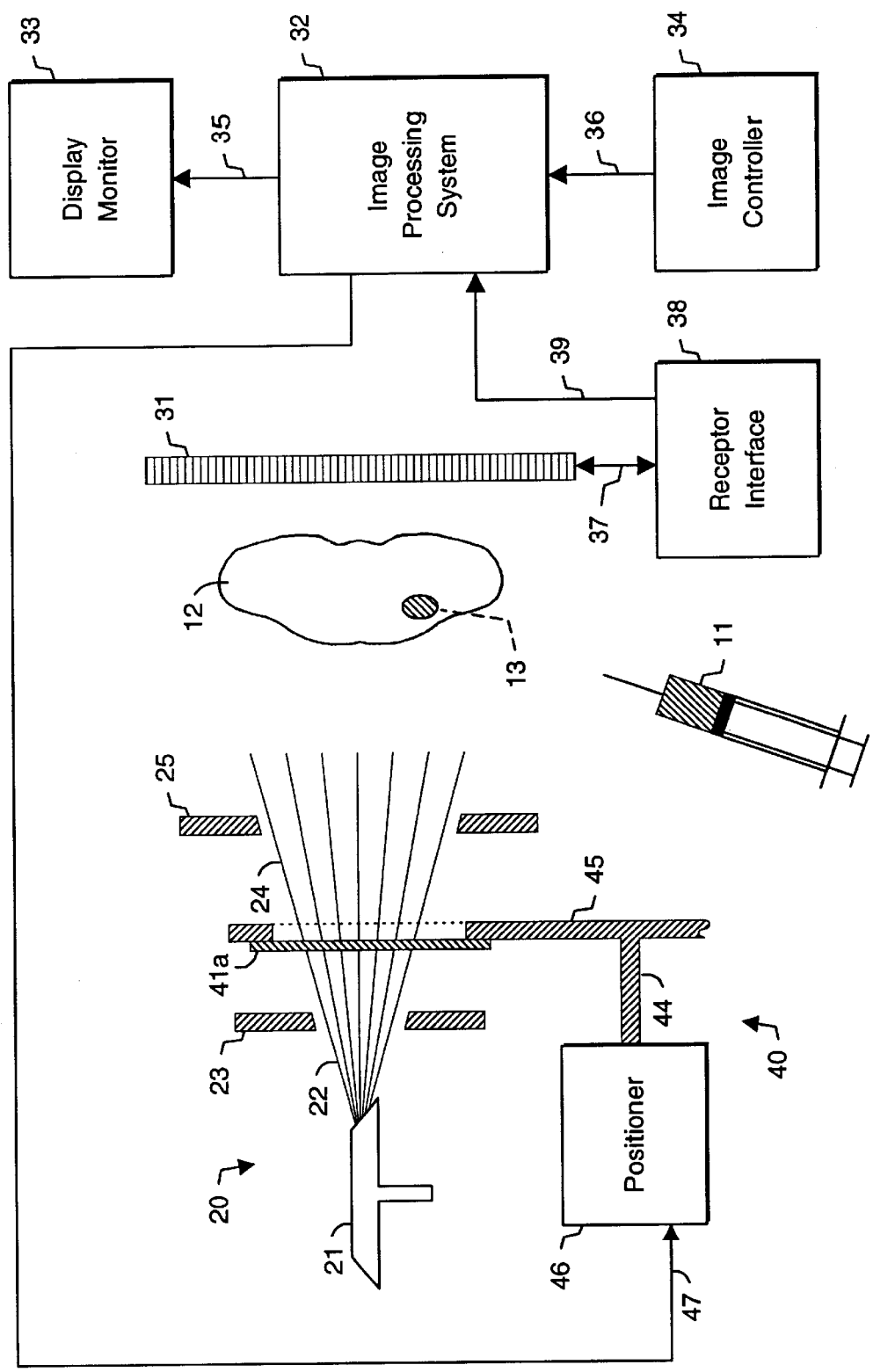
FIG. 2 is a block diagram of an embodiment of the imaging system using multiple X-ray transilluminating beams with different mean energy spectra.

A block diagram of image processing system 32 is shown in FIG. 1A. Components of the image processing system may all be contained on a single integrated circuit or distributed on multiple integrated circuits. A processor 51 may be a microprocessor, such as a Pentium Pro, or a general purpose programmable computer, or a dedicated digital signal processor (DSP) which is programmed to perform methods of the invention. The software of image processing system 32 may be stored in program memory 52, which may be ROM or RAM, or on a CD-ROM, or on a hard disk drive or on other storage media, or may be stored on processor chip 51. I/O control 55 receives digitized image data from image receptor 38 (FIGS. 1 and 2) over signal lines 39. The digitized image data is stored in image memory 54. After image processing, display controller 53 outputs the display image over signal lines 35 to a display monitor 33 (FIGS. 1 and 2).

Image processing system 32 may correct the data for linearity, converts the data to an image display format, and outputs the display image to a display monitor 33 over signal lines 35, and optionally to a hard copy device (not shown) which may be a printer. Image processing system 32 may also store the image in digital form on a hard disk, a tape drive, or another storage device (not shown).

C. Single Beam Imaging Method

If a quantity of radio-opaque imaging agent accumulates in body tissue and a radiographic image of the tissue is then acquired, the image will display the radiographic density contributed by the imaging agent combined with the radiographic density contributed by soft tissue and bone also present in the beam path. If a sufficiently large quantity of imaging agent accumulates, it may be detected and localized by direct inspection of the radiographic image. Optionally, the image may be digitized and processed using the standard methods of digital radiography, including digital filtering and contrast enhancement. If the radiographic density of the accumulated imaging agent is too low to be detected when combined with the radiographic density of soft tissue and bone, the multiple beam imaging system and method described in sections D and E may be used to isolate the radiographic density contributed by the imaging agent.

D. Multiple Beam Imaging Systems

FIG. 2 is a block diagram of a second embodiment of the imaging system, as used in a multiple beam imaging procedure performed with two or more quasi-monoenergetic X-ray transilluminating beams with different mean energy spectra. In the example of the embodiment shown in FIGS. 2, 3A, and 3B, three transilluminating beams are used.

Cell membrane-permeable radio-opaque imaging agent 11 is administered to a patient. During a predetermined time interval the imaging agent accumulates in the patient's normal body tissue 12, and in any abnormal tissue 13 that may be present.

X-ray illumination source 20, which may include an ordinary X-ray tube with a tungsten anode 21, produces continuous spectrum polyenergetic beam 22. First collimator 23 directs the beam. An X-ray filter apparatus 40 comprises a filter wheel 45, X-ray filters 41a, 42a, 43a (shown on FIG. 3B), a shaft 44, a positioner 46, and position control signals 47 generated by image processing system 32.

FIGS. 3A and 3B depict X-ray filter apparatus 40 and its relation to X-ray illumination source 20 in greater detail. Positioner 46, which may be a stepping motor whose angular shaft position is controlled by control signals 47, is mechanically coupled to filter wheel 45 through shaft 44. Control signals 47 may be generated by image processing system 32. Positioner 46 rotates the filter wheel to sequentially interpose each of filters 41a, 42b, 43c in the path of beam 22. As each of the filters is interposed in beam 22, the positioner stops rotation of the filter wheel, and a separate radiographic image is acquired. The filter wheel is then rotated to interpose the next filter in the path of beam 22.

Filter wheel 45 preferably comprises a circular mounting disc 48, made from a highly radio-opaque material, containing a plurality of cut-out apertures 41b, 42b, 43b arranged in a regularly spaced circular array. X-ray filters 41a, 42a, 43a are concentrically mounted on apertures 41b, 42b, 43b, respectively. Each X-ray filter contains a different substance that converts polyenergetic X-ray beam 22 into a quasi-monoenergetic transilluminating beam 24 with a unique mean energy spectrum. The mean energy spectrum of each filtered beam is determined by the X-ray absorption characteristics of the substance contained in the filter. The method for selection of the spectra of the beam is described in section E, and the method for selection of the filters is described in section G.

FIG. 2 shows second collimator 25, which further directs quasi-monoenergetic transilluminating beam 24 after it has passed through the X-ray filter. X-ray image receptor 31, which may be radiographic film, a film/intensifying screen combination, a stimulable phosphor storage plate, a fluoroscopic image intensifier, an amorphous silicon sensor array, a CCD/scintillator combination, or another type of X-ray sensitive receptor, acquires a radiographic image of body tissue during transillumination by beam 22. A receptor interface 38 acquires 37 the received image in a manner dependent on the type of receptor 31. If the receptor is film or a film/intensifying screen combination, the film may be processed, scanned and digitized by the interface. If the receptor is a stimulable phosphor storage plate, the plate is read out and digitized by the interface. If the receptor is a fluoroscopic image intensifier or CCD/scintillator combination, the analog output of the detector is digitized by the interface. If the receptor is an amorphous silicon sensor array, the analog output is digitized by the interface, or a digital output, if available, may be used directly. Receptor interface 38 transfers the digitized image data to image processing system 32 over signal lines 39.

A block diagram of image processing system 32 is shown in FIG. 1A. Components of the image processing system may all be contained on a single integrated circuit or distributed on multiple integrated circuits. A processor 51 may be a microprocessor, such as a Pentium Pro, or a general purpose programmable computer, or a dedicated digital signal processor (DSP) which is programmed to perform methods of the invention. The software of image processing system 32 may be stored in program memory 52, which may be ROM or RAM, or on a CD-ROM, or on a hard disk drive or other storage media, or may be stored on processor chip 51. I/O control 55 receives digitized image data from image receptor 38 (FIGS. 1 and 2) over signal lines 39. The digitized image data is stored in image memory 54. After image processing, display controller 53 outputs the display image over signal lines 35 to a display monitor 33 (FIGS. 1 and 2). I/O control 55 may also receive input signals from image controller 34 via a keyboard or mouse over signal lines 36. The image control and display methods are described in detail in section F. By means of these input signals, the viewer may switch between the display of either an anatomical or functional images, or, alternatively, display variable proportions of anatomical and functional images on a single image in registration.

Image processing system 32 linearizes the digitized data and performs an image processing procedure to enhance and display the image. (The image acquisition and processing procedures are described in section E). Image processing system 32 outputs the display image to a display monitor 33 over signal lines 35, and optionally to a hard copy device (not shown) which may be a printer. Image processing system 32 may also store the image in digital form on a hard disk, a tape drive, or another storage device (not shown).

An image controller 34, which may be a keyboard or a mouse, is connected to image processing system 32 over signal lines 36. The viewer uses image controller 34 to vary one or more of the display coefficients applied by the image processing procedure to the anatomical and functional images to be displayed. Changing the value of the display coefficients varies the degree to which imaging agent, and soft tissue and bone contribute radiographic density to the display image. The viewer may thus superimpose a variable level of the anatomical image (soft tissue and bone) on the functional image (accumulated imaging agent).

Figure 4:
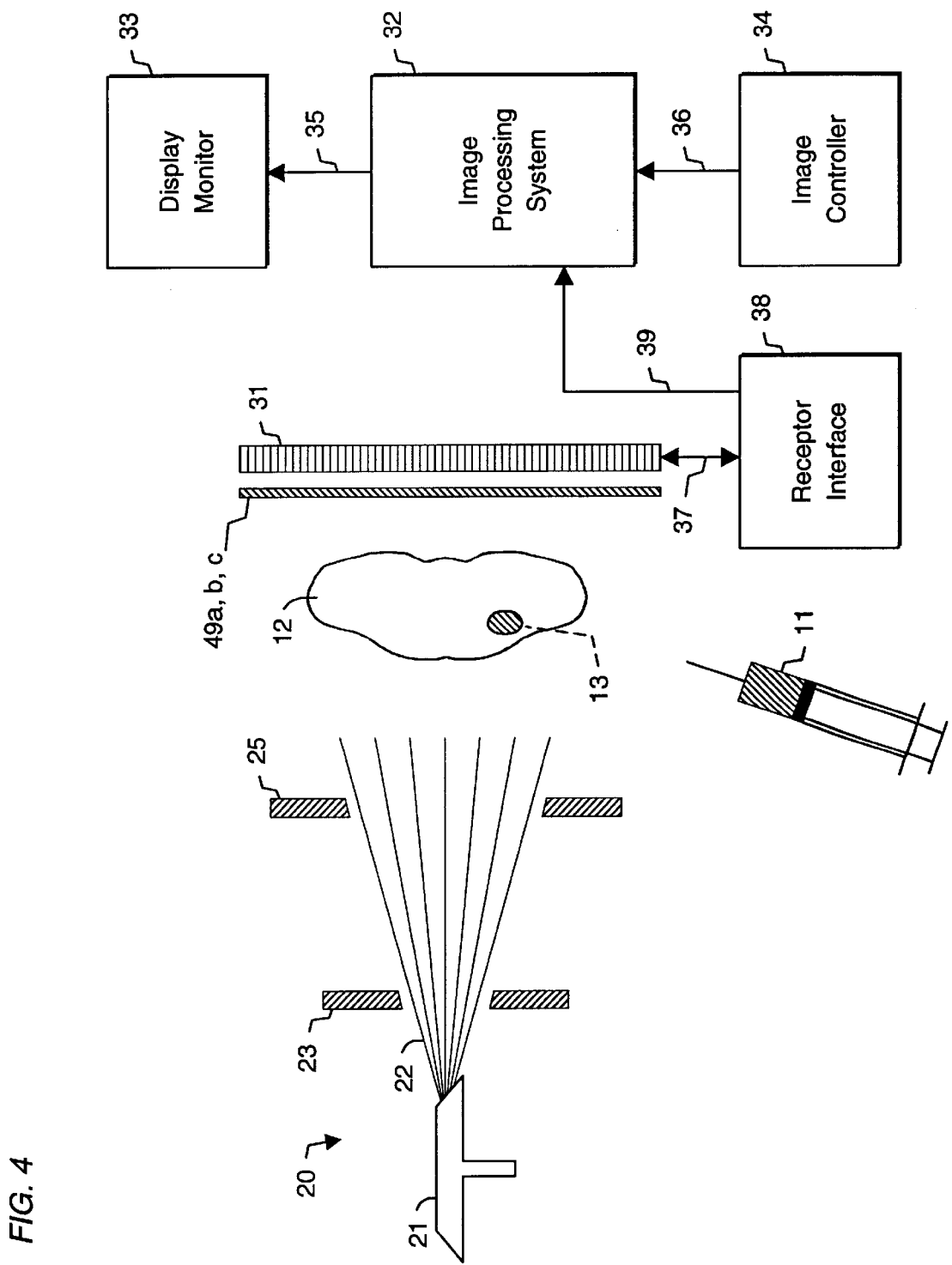
FIG. 4 is a block diagram of an embodiment of the imaging system using a single polyenergetic X-ray transilluminating beam and filtering of the beam between the patient and the image receptor.

FIG. 4 is a block diagram of a third embodiment of the imaging system, as used in a imaging procedure performed with a single, continuous spectrum, polyenergetic X-ray transilluminating beam. After the beam transilluminates the patient's body tissue, it is sequentially filtered to generate multiple beams with different mean energy spectra, and a separate radiographic image is acquired during generation of each beam.

Cell membrane-permeable radio-opaque imaging agent 11 is administered to a patient. During a predetermined time interval the imaging agent accumulates in the patient's normal body tissue 12, and in any abnormal tissue 13 that may be present.

X-ray illumination source 20, which may include an ordinary X-ray tube with a tungsten anode 21, produces continuous spectrum polyenergetic beam 22. First collimator 23 directs the beam. A second collimator 25 further directs beam 22, which transilluminates the patient's body tissue 12,13.

A series of X-ray filters 49a, b, c is interposed in temporal sequence between the patient's body tissue and image receptor 31. Each of the filters sequentially converts polyenergetic beam 22 into a quasi-monoenergetic beam with a different mean energy spectrum. In one embodiment, each X-ray filter may comprise a thin sheet of a substance with selected X-ray attenuation characteristics. This substance, which may have a K-absorption edge at a predetermined photon energy, filters the beam to enable the transmission of a predetermined energy spectrum to the image receptor. The method for selection of the spectra of the beams is described in section E, and the method for selection of the filters is described in section G.

The filter sheet may be positioned adjacent to image receptor 31, which may comprise a film/intensifying screen combination, a stimulable phosphor storage plate, a fluoroscopic image intensifier, an amorphous silicon sensor array, a CCD/scintillator combination, or another type of X-ray sensitive receptor.

Each X-ray filter contains a different substance that converts polyenergetic X-ray beam 22 into a quasi-monoenergetic beam 24 with a unique mean energy spectrum. The mean energy spectrum of each filtered beam is determined by the X-ray absorption characteristics of the substance contained in the filter. The method for selection of the spectra of the beam is described in section E, and the method for selection of the filters is described in section G.

X-ray image receptor 31, which may be radiographic film, a film/intensifying screen combination, a stimulable phosphor storage plate, a fluoroscopic image intensifier, an amorphous silicon sensor array, a CCD/scintillator combination, or another type of X-ray sensitive receptor, acquires a radiographic image of body tissue during transillumination by beam 22. A receptor interface 38 acquires 37 the received image in a manner dependent on the type of receptor 31. Subsequent acquisition and processing of the radiographic images are similar to those described earlier in this section for the multiple beam imaging system using the filter wheel apparatus.

In one embodiment of the multiple beam imaging system, the requirement for a sequence of transilluminating X-ray beams with different mean energy spectra is satisfied by filtration of a polyenergetic beam, in temporal sequence, through substances with selected X-ray absorption characteristics. However, it will be obvious to one skilled in the art that this requirement may also be satisfied by other means. For example, an X-ray monochromator may be sequentially tuned to produce monoenergetic beams with the required energy spectra. Alternatively, a tuned synchrotron may be used to produce monoenergetic beams with the required spectra.

E. Multiple Beam Imaging Method

If a quantity of radio-opaque imaging agent accumulates in body tissue and a radiographic image of the tissue is then acquired, the image will display the radiographic density contributed by the imaging agent combined with the radiographic density contributed by soft tissue and bone also present in the beam path. If a small quantity of imaging agent accumulates in the tissue being examined, visualization of the imaging agent should be enhanced. The radiographic density it contributes to the image should therefore be isolated and selectively displayed. A number of approaches to this problem have been described [Kelcz F, Mistretta C A: Med. Phys. 3: 159–168 (1976); Kelcz F et al.: Med. Phys. 4: 26–35 (1977); Riederer S J et al.: Med. Phys. 8: 471–479 (1981); Riederer S J et al.: Med. Phys. 8: 480–487 (1981); Macovski A et al.: Med. Phys 6: 53–58 (1979)].

The multiple beam imaging method generates a radiographic image which emphasizes the radiographic density of accumulated imaging agent and almost completely cancels the radiographic density of the soft tissue and bone present in the beam path. To enhance the image in this manner, body tissue being examined is sequentially transilluminated by two or more beams with different preselected mean energy spectra, and a separate image is acquired during transillumination by each beam. The separate acquired images are then combined, using image weighting coefficients, into a single image.

The transilluminating beams may be quasi-monoenergetic or monoenergetic, and their spectra are selected based on the K-absorption edge of the radio-opaque element contained in the imaging agent.

For each element in the periodic table there is a unique profile of X-ray attenuation over the photon energy spectrum, and, most importantly, a characteristic energy at which X-ray attenuation sharply increases. This abrupt increase in attenuation is known as the K-absorption edge. The K-absorption edge for each element is unique, and is monotonically related to the atomic number of the element.

In one embodiment of a multiple beam imaging method, one beam is selected to have a mean energy spectrum just below the K-absorption edge of the radio-opaque element in the imaging agent, and a second beam is selected to have a mean energy spectrum just above the K-absorption edge of the radio-opaque element.

The principle of operation of the method is illustrated in the following example. Assume that a quantity of radio-opaque imaging agent has accumulated in an area of body tissue under examination. The tissue is first transilluminated by beam $E_1$ with a mean energy spectrum just below the K-absorption edge of the radio-opaque element in the imaging agent, and image $X_1$ is acquired. Absorption of beam $E_1$ by the imaging agent will be relatively low, and the radiographic density it contributes to image $X_1$ will be correspondingly high.

The tissue is then transilluminated by beam $E_2$ with a mean energy spectrum just above the K-absorption edge of the radio-opaque element in the imaging agent, and image $X_2$ is acquired. Because there is a sharp increase in X-ray attenuation at the K-absorption edge of the element, absorption of beam $E_2$ by the imaging agent will be relatively high, and the radiographic density it contributes to image $X_2$ will be correspondingly low.

Soft tissue will contribute a nearly equal level of radiographic density to image $X_1$ and to image $X_2$. This is because the K-absorption edges of the elements which comprise soft tissue (predominantly carbon, hydrogen, oxygen, and nitrogen), are located well below the mean energy spectra of beams $E_1$ and $E_2$. Thus, the absorption of beams $E_1$ and $E_2$ by soft tissue will be nearly equivalent.

Bone will also contribute a nearly equal level of radiographic density to image $X_1$ and to image $X_2$. This is because the K-absorption edges of the elements which comprise bone (predominantly carbon, hydrogen, oxygen, nitrogen, and calcium) are likewise located well below the mean energy spectra of beams $E_1$ and $E_2$. Thus, the absorption of beams $E_1$ and $E_2$ by bone will be nearly equivalent.

If image $X_2$ is then subtracted from image $X_1$ to produce image Z, the relatively large difference between the radiographic density contributed by the accumulated imaging agent in images $X_1$ and $X_2$ will result in a relatively high level of residual radiographic density in subtracted image Z. The approximately equal levels of radiographic density contributed by soft tissue to images $X_1$ and $X_2$ and by bone to images $X_1$ and $X_2$ will result in relatively low levels of residual radiographic density in subtracted image Z. Thus, by computing the difference image of images $X_1$ and $X_2$, the radiographic density of imaging agent is preserved in the resulting image Z, and the radiographic density of soft tissue and bone is essentially canceled.

A viewer may switch between a display showing image Z, and an anatomical image (e.g. image $X_1$) which is aligned in registration with image Z. In this manner, the anatomical and functional tissue images may be separately viewed. Alternatively, image Z may be combined with image $X_1$ or image $X_2$, in registration, to produce a single anatomical and functional image.

In practice, the attenuation of beams $E_1$ and $E_2$ by soft tissue are not exactly equal. Likewise the attenuation of beams $E_1$ and $E_2$ by bone are not exactly equal. A residual level of radiographic density due to soft tissue and bone therefore remains after subtraction of image $X_2$ from image $X_1$. To optionally compensate for these residuals, a third beam $E_3$ may be generated with a mean energy spectrum well above the mean energy spectrum of beam $E_2$, and a third image $X_3$ acquired during transillumination of the tissue by beam $E_3$. Appropriate weighting of image $X_3$, and its combination with weighted images $X_1$ and $X_2$, produces a display image Z with almost complete cancellation of the radiographic density of soft tissue and bone.

When a quasi-monoenergetic beam traverses a length of soft tissue and bone, its mean energy spectrum slightly increases. This phenomenon is known as beam hardening, and, if uncorrected, may reduce the degree of cancellation of soft tissue and bone in the displayed image. Accordingly, in one embodiment of the multiple beam imaging method, additional higher order terms may be applied as weighting coefficients to images $X_1$, $X_2$, and $X_3$ to compensate for beam hardening and further improve the cancellation of soft tissue and bone on the displayed image.

In summary, by the general method of:

1) administering a bidirectionaly cell membrane-permeable, radio-opaque imaging agent to a patient;
2) allowing an interval for accumulation of the imaging agent in body tissue;
3) sequentially transilluminating the tissue under examination with multiple X-ray beams $E_1, \ldots, E_n$ with different mean energy spectra;
4) acquiring a separate radiographic image $X_1, \ldots, X_n$ during transillumination by each beam;
5) multiplying the acquired images $X_1, \ldots, X_n$ by weighting coefficients $w_1, \ldots, W_n$ respectively, and optionally multiplying images $X_1^1, \ldots, X_n^2$, by weighting coefficients $h_1, \ldots, h_n$ to compensate for beam hardening during tissue transillumination;
6) adding all weighted images to produce a display image Z;

the relative contributions of the radio-opaque imaging agent, soft tissue, and bone to radiographic density on display image Z may be computed and isolated. By the additional step of:

7) displaying a viewer-controlled fraction of display image Z together with a fraction of any one of images $X_1, \ldots, X_n$, a variable proportion of the functional and anatomical images of the tissue being examined may be displayed, with both images in complete registration.

A flow chart of the image acquisition and processing procedure 80 is shown in FIG. 8. A radio-opaque functional imaging agent is administered 81 to a patient. During a predetermined time interval 82 the imaging agent accumulates in the patient's body tissue. The patient is then positioned 83 appropriately between the X-ray source and image receptor.

An X-ray beam $E_1$ transilluminates 84 the body tissue being examined, and a radiographic image $R_1$ is acquired 85. The sequence of transillumination and image acquisition is repeated 86 for beam $E_2$ and image $R_2$, and beam $E_3$ and image $R_3$, respectively.

The following image processing procedure is performed on each radiographic image in sequence. Radiographic image $R_1$ is digitized 87 to generate digital image $D_1$. The radiographic image may be digitized immediately after acquisition of each image, digitized after acquisition of the entire series of images, or stored for digitization at some later time. After digitization, image processing may be performed immediately, or the digital arrays may be stored in random-access memory, on a hard drive, on tape, or on other digital storage media for later processing. Thus, $$D_1 = \text{digitized } R_1$$

Corrections to linearize the transfer function of the X-ray image receptor may then be applied 88 to the digital array. The correction may be implemented by one or more hardware-based lookup tables. The input to the lookup tables may be the uncorrected output value of the analog-to-digital converter and the output of the lookup table would then be the linearized. Alternatively, the correction may be performed in software by one or more lookup tables stored in random-access memory, on a hard disk, or on other storage media. Thus, $$D'_1 = \text{corrected } D_1$$

A number of image receptor systems are now available and others are being developed for acquiring radiographic images in a form suitable for digital processing. These receptor systems include, but are not limited to, stimulable phosphor storage plates, fluoroscopic image intensifiers, amorphous silicon sensor arrays, and CCD/scintillator combinations. For clarity in the description of the image processing procedure, it is assumed that the image receptor used in the present invention is characterized by a) a substantially linear relationship between X-ray photon energy input and detector signal output, and b) a substantially linear detector response in the photon energy spectrum between approximately 10 keV and approximately 60 keV. If an image receptor with nonlinear gain or spectral response characteristics is used in the present invention, the nonlinearity may be appropriately corrected by hardware or software. The correction is based on the predetermined response of the image receptor to the range of photon input levels and energy spectra used in the imaging procedure. The image array is therefore assumed to have a linear relationship to the input X-ray signal after correction 88. The modifications necessary to achieve this correction are mathematically straightforward, and will be evident to one of ordinary skill in the art.

After digitization and correction, the natural logarithm ln of the value of each pixel in the digital image D; is computed 89 to generate image $X_1$ $$X_1 = \ln D'_1$$

Image processing system 32 multiplies 90 each pixel value in image $X_1$ by weighting coefficient $w_1$. In one embodiment an additional higher order term may be added to compensate for the slight beam hardening, or increase in mean beam energy, and resulting small decrease in effective mass attenuation coefficient that occurs when each quasi-monoenergetic beam passes through a thickness of tissue or bone. This term is equal to $X_1^2$ multiplied by hardening coefficient $h_1$. The entire image weighting term function is $$Y_1 = (X_1 w_1) + (X_1^2 h_1)$$

Figure 9:
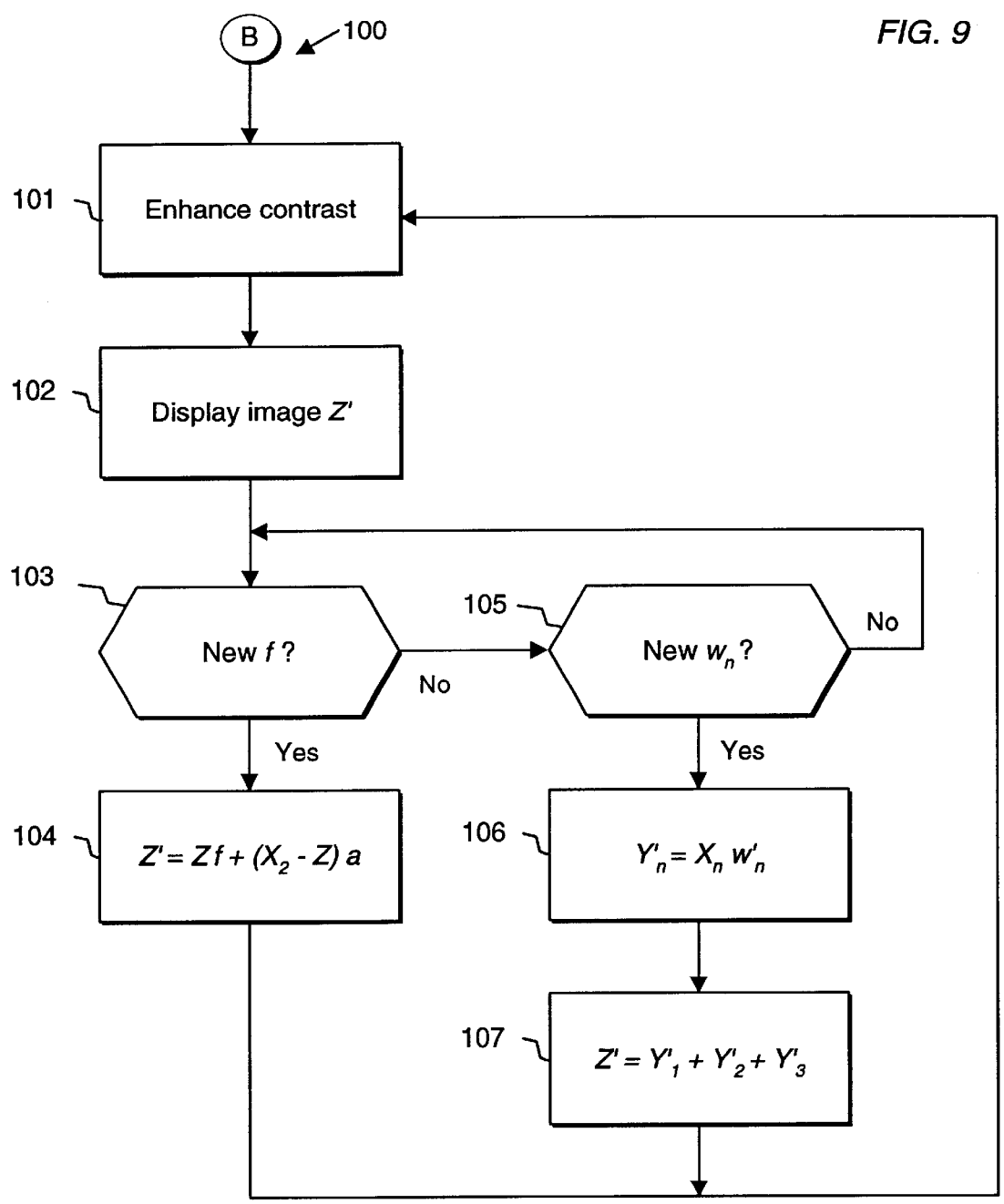
FIG. 9 is a flow chart of the image control and display procedure.

Image digitization, correction, log conversion, and image weighting is repeated 91 for radiographic images $R_2$ and $R_3$. The image combination formula, which in one embodiment is $$Z = Y_1 + Y_2 + Y_3$$

is then performed 92 to yield display image Z. Image Z is displayed 93 on the display monitor, as shown in FIG. 9. As described in section F below, image Z may be modified by the user to display varying proportions of imaging agent, soft tissue and bone present in the beam path. Image Z may also be converted to hard copy, and may be stored in random-access memory, on a hard drive, on tape, or on another digital storage medium for archiving and for later viewing.

Table 2 shows the mean energy spectra for beams $E_1$, $E_2$, and $E_3$, the corresponding image weighting coefficients $w_1$, $w_2$, and $w_3$, and hardening coefficients $h_1$, $h_2$, and $h_3$ used in one embodiment of the multiple beam imaging method. These coefficients are used in the image weighting step 90 of FIG. 8.

TABLE 2

| Beam | keV | Image | w | h |
|---|---|---|---|---|
| $E_1$ | 31.05 | $X_1$ | −30.5 | 0.11 |
| $E_2$ | 37.10 | $X_2$ | 99.7 | −0.43 |
| $E_3$ | 44.10 | $X_3$ | −67.4 | 0.25 |

Table 3 shows typical concentrations of imaging agent, soft tissue and bone present in the transilluminating X-ray beam path and their attenuation of beams $E_1$, $E_2$, and $E_3$. The table also shows levels of radiographic density present on acquired images $X_1$, $X_2$ and $X_3$, and the radiographic density present on display image Z after application of the image processing procedure described above.

TABLE 3

| Image component | Thickness gm/cm$^2$ | Beam Transmittance | | | Relative density |
|---|---|---|---|---|---|
| | | $E_1$ | $E_2$ | $E_3$ | |
| Iodine | 0.001 | 99.03 | 97.68 | 98.35 | 1.000 |
| Soft tissue | 12.000 | 69.42 | 74.93 | 78.91 | 0.009 |
| Bone | 3.000 | 24.85 | 40.11 | 58.27 | 0.039 |

F. Image Control and Display Methods

A flow chart of the image control procedure 100 is shown in FIG. 9. The weighted and combined image Z resulting from step 92 (FIG. 8) is an image of relatively low visual contrast. A contrast enhancement procedure, such as a level shift and histogram stretch, may be first performed 101 to enhance the visual contrast of image Z, to produce image Z'.

After completion of the image acquisition and processing procedure, each of unweighted, uncombined images $X_1$, $X_2$ and $X_3$ is an anatomical image, represented by radiographic density contributed by soft tissue and bone, and also containing radiographic density contributed by accumulation of the radio-opaque imaging agent. Weighted and combined image Z is solely a functional image. The viewer may interactively vary the displayed proportions of the anatomical and functional images, and the combined images will be displayed on a single image in complete registration. Display coefficients represents the displayed proportion of the functional image, and display coefficient α, which is forced to (1−f), represents the displayed proportion of the anatomical image. In one embodiment, the value of f is initially set at 1.0 when a new image Z' is displayed, so that only the functional image is first displayed. While image Z' is displayed 102 on the display monitor, image processing system 32 (FIG. 2) periodically tests 103 for a change in coefficient f, which the viewer selects using image controller 34 (FIG. 2). When a change is detected in coefficient f, the image processing system combines 104 the selected proportions of functional image Z and image $X_1$, performs contrast enhancement, and redisplays 102 the resulting new image Z' on the display monitor. Image Z' may also be stored in random-access memory, on a hard drive, or on another storage device.

While viewing the displayed image, the viewer may thereby interactively superimpose a variable proportion of the anatomical image on the functional image. Since the anatomical and functional images are displayed in complete registration, this capability facilitates precise localization of malignant tissue, or other tissue which is labeled by the imaging agent, with reference to nearby anatomical landmarks.

A small unwanted residual density contributed by soft tissue or bone may remain on display image Z after image processing using the predetermined weighting coefficients used in the image processing procedure described in section E. The viewer may interactively adjust the image weighting coefficient of image $X_3$ to completely cancel this residual.

While image Z' is displayed 102 on the display monitor, image processing system 32 (FIG. 2) periodically tests 105 for a change in weighting coefficient $w_3$, which is controlled by the viewer using image controller 34 (FIG. 2). A change in the value of weighting coefficient $w_3$ changes the contribution of image $Y_3$ to display image Z, and therefore the degree to which soft tissue and bone are canceled in image Z. When a change in the weighting coefficient is detected, the image processing system recomputes the image 106, 107 using the new coefficient $w_3$ performs contrast enhancement 101 to stretch the recomputed image to full scale, and displays 102 the recomputed image Z' on the display monitor.

G. X-ray Filter Apparatus

Different approaches may be used to generate the quasi-monoenergetic or monoenergetic X-ray beams required for the multiple beam imaging method. In one embodiment of the present invention, an X-ray filter apparatus sequentially generates multiple quasi-monoenergetic beams with different mean energy spectra. However, alternative methods for generating multiple quasi-monoenergetic or monoenergetic X-ray beams, each having a unique energy spectrum, may be also be used with the present invention.

Operation of the filter apparatus is based on the principle that a polyenergetic X-ray beam may be converted into a quasi-monoenergetic beam, with a unique mean energy spectrum, by filtering the polyenergetic beam through a substance containing an element with selected X-ray attenuation characteristics. Specifically, a substance with a K-absorption edges at a selected photon energy is used to generate a beam with the desired energy spectrum.

Figure 5A:
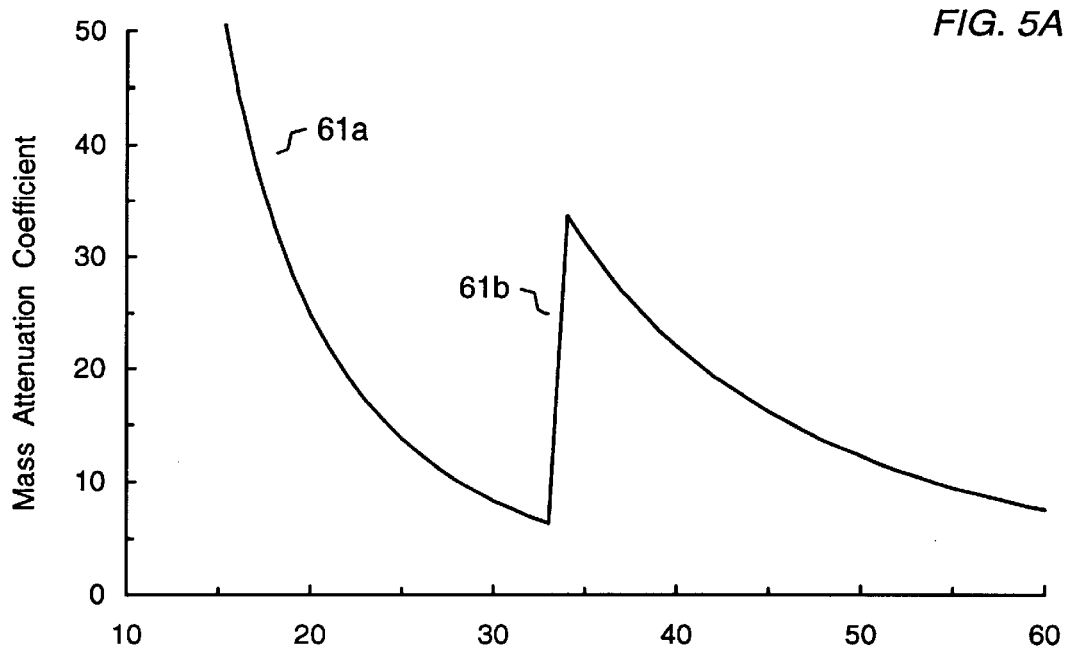
FIG. 5A shows the mass attenuation coefficient of iodine as a function of photon energy.

As described previously, for each element in the periodic table there is a characteristic photon energy at which X-ray attenuation sharply increases. This abrupt increase in attenuation is known as the K-absorption edge. An example of a K-absorption edge is shown in FIG. 5A. A graph 61a of the mass attenuation coefficient of iodine (I, Z=53) is plotted as a function of photon energy from 10 to 60 keV. K-absorption edge 61b appears as an abrupt increase in the mass attenuation coefficient at 33.1 keV.

Each X-ray filter 41a, 42a, and 43a (FIG. 3B) contains a different substance which transforms polyenergetic X-ray beam 22 into a quasi-monoenergetic transilluminating beam 24 with a unique mean energy spectrum.

As noted in section E, the mean energy spectrum of transilluminating beam $E_1$ should be just below the K-absorption edge of the radio-opaque element whose radiographic density is to be isolated. The mean energy spectra of beam $E_2$ should be above the K-absorption edge of the radio-opaque element. In one embodiment, a third transilluminating beam $E_3$ is used and should have a mean energy spectrum above that of beam $E_2$. In one embodiment of the imaging agent in the present invention, the radio-opaque element used is iodine. In this case, substances which may be used to filter polyenergetic beams to convert them into quasi-monoenergetic beams with appropriate mean energy spectra include iodine, cerium, and brass. The X-ray filters may be implemented with cylindrical cells containing solutions of the substances selected for beam filtration, or with solid disks of metal. The required concentrations of the filter substances in solution and the thicknesses of the solid metal filters are readily calculated using their mass attenuation coefficients.

Attenuation of an X-ray beam by passage through a substance is described by the exponential attenuation law:

$$I(E)/I_0(E)=exp[-(\mu/\rho)\, x]$$

where I(E) is the output intensity of the beam, $I_0(E)$ is the incident intensity of the beam, and $\mu$ is the attenuation coefficient of the substance at energy E. $\rho$ is the density of the substance, and x is the mass thickness (mass per unit area) of the substance.

FIGS. 5A through 7B show the X-ray mass attenuation coefficients of iodine, cerium, and brass plotted vs. photon energy, and the conversion of polyenergetic X-ray beams to quasi-monoenergetic beams with different mean energy spectra by filters containing selected thicknesses of these substances.

FIG. 5A shows a graph 61a of the mass attenuation coefficient of iodine (I, Z=53) as a function of photon energy. The K-absorption edge 61b of iodine is at 33.1 keV.

Figure 5B:
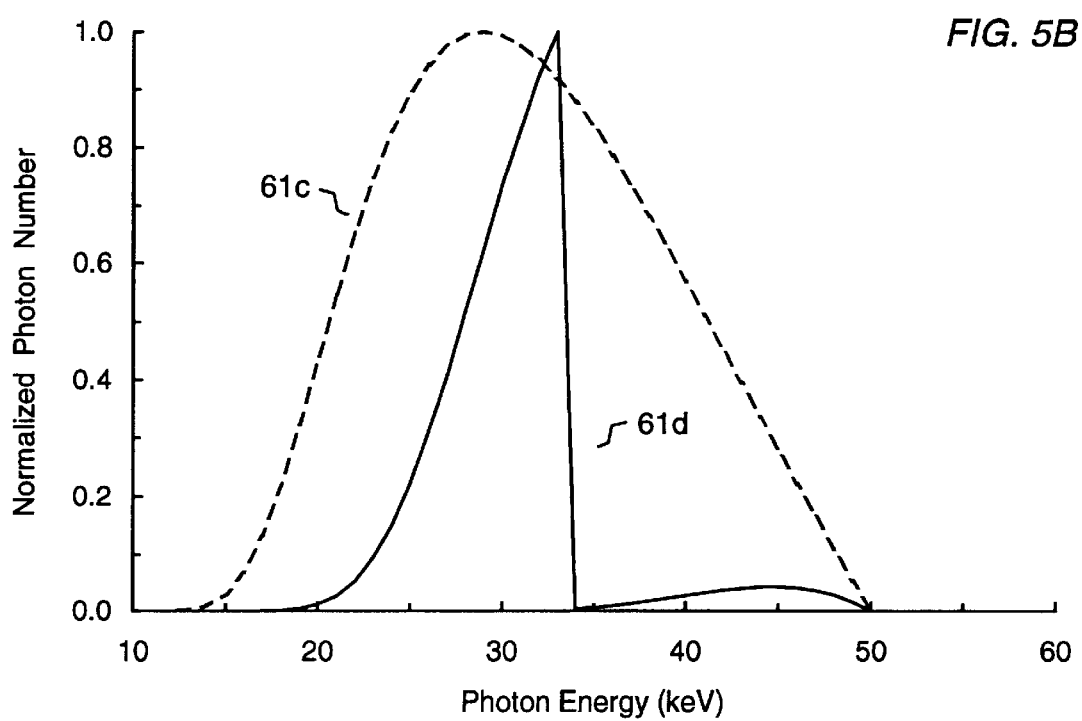
FIG. 5B shows the energy spectra of unfiltered and iodine-filtered X-ray beams.

FIG. 5B shows normalized energy spectra of unfiltered and iodine-filtered X-ray beams. Graph 61c (dashed line) shows the spectrum of an unfiltered beam generated by a tungsten anode source operated at 50 kVp. X-ray filter 41a (FIG. 3B) contains a solution of an iodine compound in which the mass thickness of iodine is 0.200 gm/cm². A polyenergetic 50 kVp beam with spectrum 61c is converted by this filter to a quasi-monoenergetic beam with spectrum 61d, as shown in FIG. 5B. Spectrum 61c of the unfiltered beam is polyenergetic and relatively broad. In contrast, the spectrum of iodine-filtered beam 61d is narrower and quasi-monoenergetic. Iodine-filtered beam 61d has an energy peak at 33 keV and a mean energy spectrum of 31.1 keV.

Figure 6A:
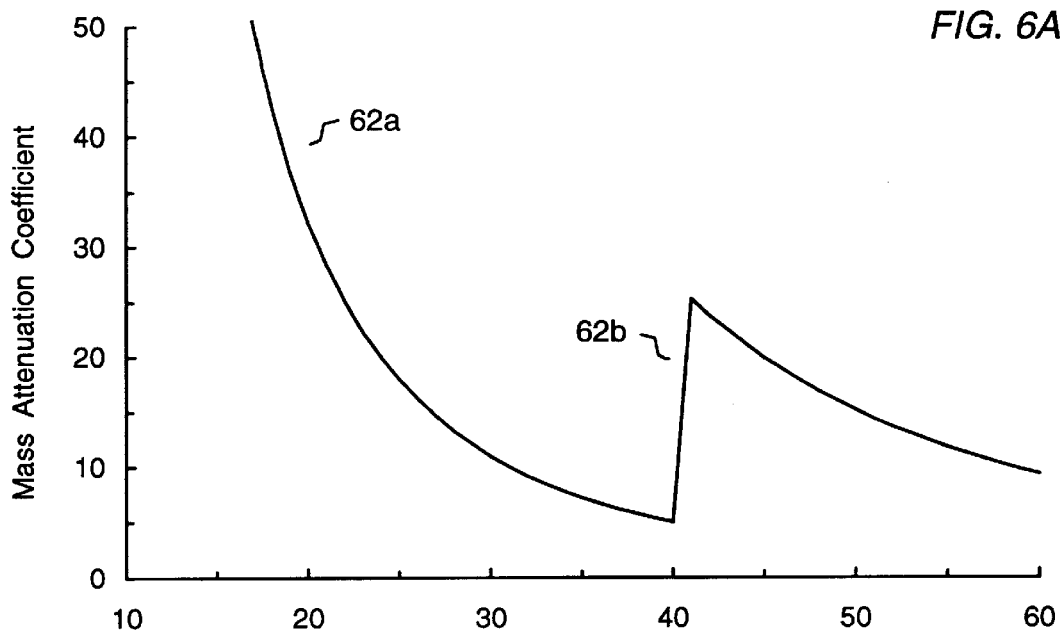
FIG. 6A shows the mass attenuation coefficient of cerium as a function of photon energy.

FIG. 6A shows a graph 62a of the mass attenuation coefficient of cerium (Ce, Z=58) as a function of photon energy. The K-absorption edge 62b of cerium is at 40.0 keV.

Figure 6B:
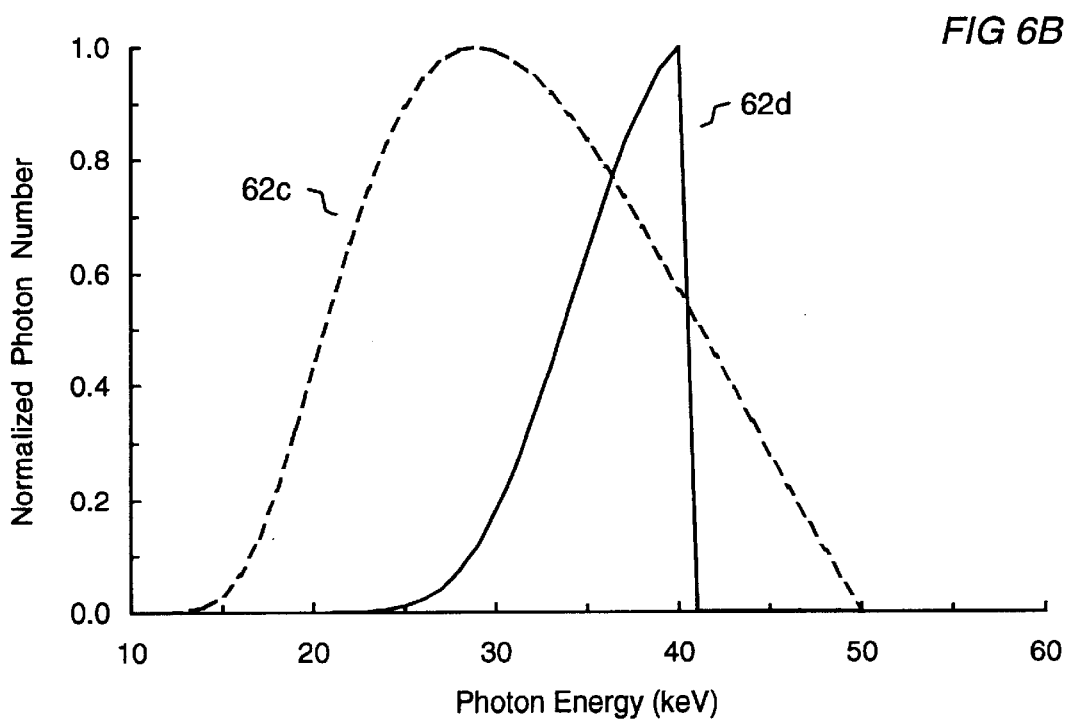
FIG. 6B shows the energy spectra of unfiltered and cerium-filtered X-ray beams.

FIG. 6B shows normalized energy spectra of unfiltered and cerium-filtered beams. X-ray filter 42a contains a solution of a cerium compound in which the mass thickness of cerium is 0.380 gm/cm². A polyenergetic 50 kVp beam with spectrum 62c is converted by this filter to a quasi-monoenergetic beam with spectrum 62d, as shown in FIG. 6B. Cerium-filtered beam 62d has an energy peak at 40 keV and a mean energy spectrum of 36.6 keV.

Figure 7A:
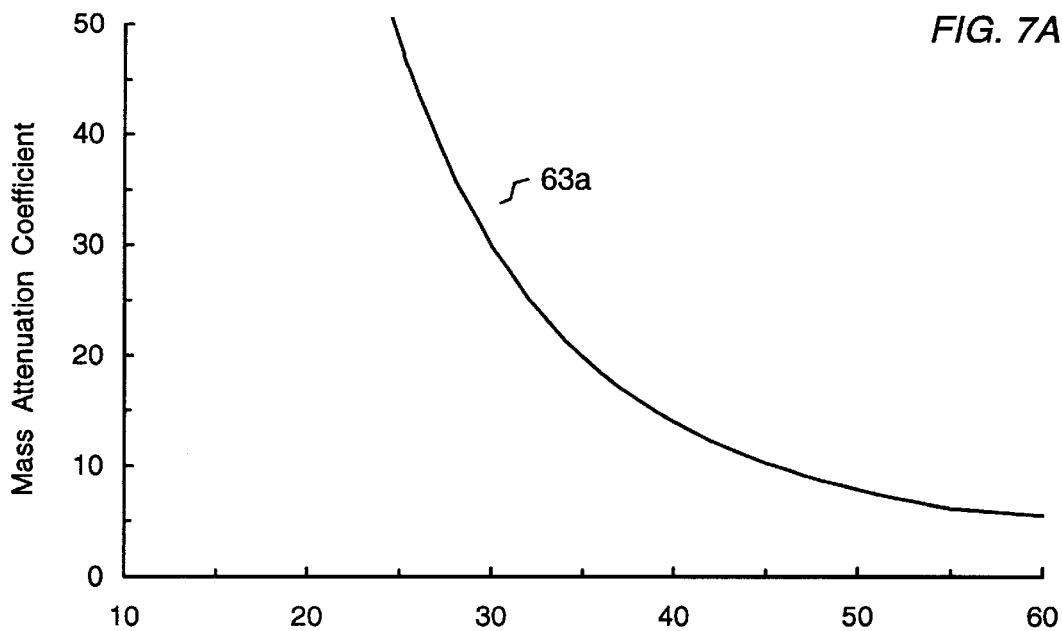
FIG. 7A shows the mass attenuation coefficient of brass as a function of photon energy.

FIG. 7A shows a graph 63a of the mass attenuation coefficient of brass as a function of photon energy. One K-absorption edge of brass is at 8.97 keV (Cu, Z=29) (not shown) and a second K-absorption edge is at 9.65 keV (Zn, Z=30) (not shown).

Figure 7B:
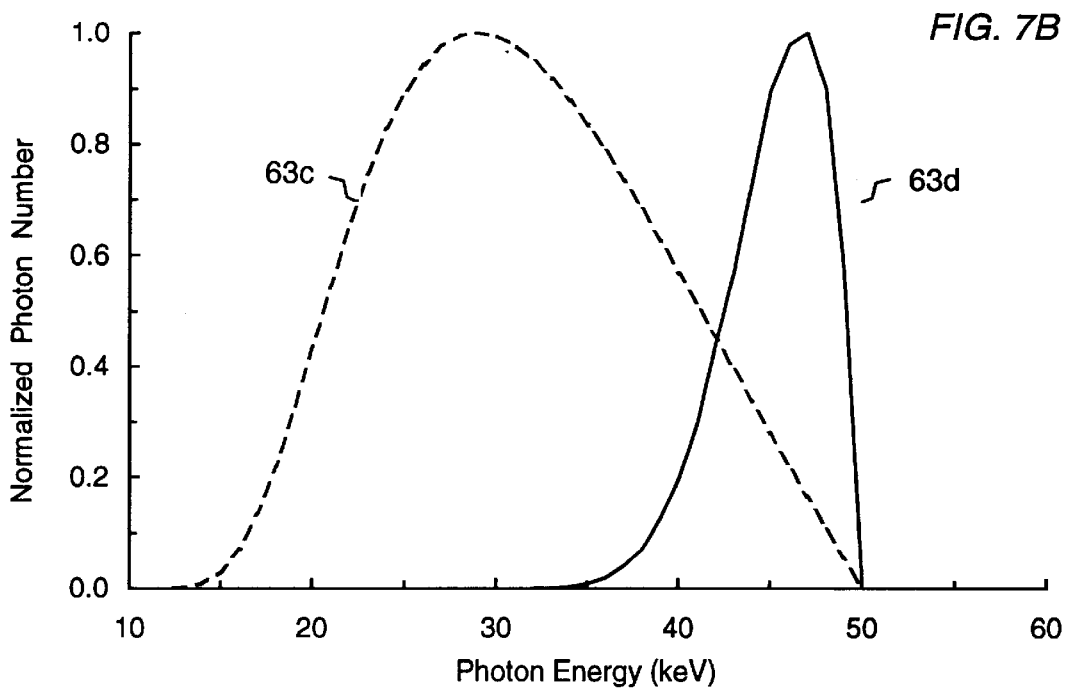
FIG. 7B shows the energy spectra of unfiltered and brass-filtered X-ray beams.

FIG. 7B shows normalized energy spectra of unfiltered and brass-filtered beams. X-ray filter 43a is a thin circular brass disc in which the mass thickness of brass is 1.500 gm/cm². A polyenergetic 50 kVp beam with spectrum 63c is converted by this filter to a quasi-monoenergetic beam with spectrum 63d, as shown in FIG. 7B. Brass-filtered beam 63d has an energy peak at 46 keV and a mean energy spectrum of 45.3 keV.

Table 4 summarizes the filtration parameters for generation of each of the quasi-monoenergetic transilluminating beams from a 50 kVp polyenergetic input beam and the energy characteristics of the filtered beams used to generate display image Z as described in section E.

TABLE 4

| Beam | Filter substance | Thickness gm/cm² | Beam mean E |
|---|---|---|---|
| $E_1$ | Iodine | 0.200 | 31.05 |
| $E_2$ | Cerium | 0.380 | 37.00 |
| $E_3$ | Brass | 1.340 | 45.01 |

It should be understood that the values presented here are only representative and are given as examples. The specific filter thicknesses, beam energies and image weighting coefficients may be varied widely depending on the particular conditions of the imaging procedure. The method for calculation of these values will be apparent to one of ordinary skill in the art.

Having now fully described the invention, it will be apparent to one of ordinary skill in the art that many changes and modifications can be made thereto without departing from the spirit or scope of the invention as set forth herein.

I claim:

1. A system for radiographic imaging of body tissue comprising:
    a) a cell membrane-permeable, radio-opaque imaging agent;
    b) means for administering said imaging agent to a patient;
    c) means for generating a plurality of X-ray beams with predetermined different energy spectra;
    d) means for acquiring radiographic images disposed on the side of said patient opposite said X-ray beam generating means; and
    e) means for performing a weighted combination of a plurality of said radiographic images to produce a single image.

2. The system of claim 1 wherein said plurality of beams are quasi-monoenergetic.

3. The system of claim 1 wherein said plurality of beams are monoenergetic.

4. The system of claim 1 wherein 2 beams are generated.

5. The system of claim 1 wherein more than 2 beams are generated.

6. The system of claim 1, further including means for displaying variable proportions of radiographic density contributed by said imaging agent, soft tissue, and bone to said single image.

7. The system of claim 1 wherein said cell membrane-permeable, radio-opaque imaging agent selectively binds to a cellular target.

8. The system of claim 7 wherein said cellular target is a cellular structure.

9. The system of claim 7 wherein said cellular target is a molecule.

10. The system of claim 7 wherein said cellular target is selected from the group of proteins, nucleic acids, coenzymes, and lipids.

11. The system of claim 7 wherein said cellular target is an enzyme.

12. The system of claim 7 wherein said cellular target is hexokinase.

13. The system of claim 1 wherein said imaging agent accumulates in malignant tissue at a different rate than in non-malignant tissue.

14. The system of claim 1 wherein said imaging agent accumulates in abnormal myocardial tissue at a different rate than in normal myocardial tissue.

15. The system of claim 1 wherein said imaging agent has a logP of above 0.0.

16. A system for radiographic imaging of body tissue comprising:
    a) a radio-opaque imaging agent which is capable of entering a cell through passive diffusion and which selectively binds to a cellular target;
    b) means for administering said imaging agent to a patient;
    c) means for generating an X-ray beam; and
    d) means for acquiring radiographic images disposed on the side of said patient opposite said X-ray beam generating means.

17. The system according to claim 16, wherein the means for generating said X-ray beam is capable of generating a plurality of beams with predetermined different energy spectra and further comprising means for performing a weighted combination of a plurality of said radiographic images to produce a single image.

18. The system of claim 17 wherein said plurality of beams are quasi-monoenergetic.

19. The system of claim 17 wherein said plurality of beams are monoenergetic.

20. The system of claim 17 wherein 2 beams are generated.

21. The system of claim 17 wherein more than 2 beams are generated.

22. The system of claim 17 wherein said means for generating said plurality of beams with predetermined different energy spectra is disposed between said means for generating an X-ray beam and said patient.

23. The system of claim 17 wherein said means for generating said plurality of beams with predetermined different energy spectra is disposed between said patient and said means for acquiring radiographic images.

24. The system of claim 17, further including means for displaying variable proportions of radiographic density contributed by said imaging agent, soft tissue, and bone to said single image.

25. The system of claim 16 wherein said cellular target is a cellular structure.

26. The system of claim 16 wherein said cellular target is a molecule.

27. The system of claim 16 wherein said cellular target is selected from the group of proteins, nucleic acids, coenzymes, and lipids.

28. The system of claim 16 wherein said cellular target is an enzyme.

29. The system of claim 16 wherein said cellular target is hexokinase.

30. The system of claim 16 wherein said imaging agent accumulates in malignant tissue at a different rate than in non-malignant tissue.

31. The system of claim 16 wherein said imaging agent accumulates in abnormal myocardial tissue at a different rate than in normal myocardial tissue.

32. The system of claim 16 wherein said imaging agent has a logP of above 0.0.

33. A method for radiographic imaging of body tissue comprising:
    a) administering to a live organism containing tissue a bidirectionally cell membrane-permeable, radio-opaque imaging agent,
    b) generating an X-ray beam;
    c) illuminating said tissue with said X-ray beam; and
    d) acquiring a radiographic image of said tissue during illumination.

34. The method of claim 33, further including:
a) generating a plurality of X-ray beams with predetermined different energy spectra;
b) illuminating said tissue with each of said plurality of beams;
c) acquiring a radiographic image of said tissue during illumination by each of said plurality of beams; and
d) performing a weighted combination of a plurality of said radiographic images to produce a single image.

35. The method of claim 34 wherein said plurality of beams are monoenergetic.

36. The method of claim 34 wherein said plurality of beams are quasi-monoenergetic.

37. The system of claim 34 wherein 2 beams are generated.

38. The system of claim 34 wherein more than 2 beams are generated.

39. The method of claim 34, further displaying variable proportions of radiographic density contributed by said imaging agent, soft tissue, and bone to said single image.

40. The method of claim 33 wherein said cell membrane-permeable, radio-opaque imaging agent selectively binds to a cellular target.

41. The method of claim 40 wherein said cellular target is a cellular structure.

42. The method of claim 40 wherein said cellular target is a molecule.

43. The method of claim 40 wherein said cellular target is selected from the group of proteins, nucleic acids, coenzymes, and lipids.

44. The method of claim 40 wherein said cellular target is an enzyme.

45. The method of claim 40 wherein said cellular target is hexokinase.

46. The method of claim 33 wherein said imaging agent accumulates in malignant tissue at a different rate than in non-malignant tissue.

47. The method of claim 33 wherein said imaging agent has a logP of above 0.0.

48. A method for radiographic imaging of body tissue comprising:
a) administering to a live organism containing tissue a cell membrane-permeable, radio-opaque imaging agent which selectively binds to an intracellular target in the organism;
b) generating an X-ray beam;
c) illuminating said tissue with said X-ray beam; and
d) acquiring a radiographic image of said tissue during illumination.

49. The method of claim 48, further including:
a) generating a plurality of X-ray beams with predetermined different energy spectra;
b) illuminating said tissue with each of said plurality of beams;
c) acquiring a radiographic image of said tissue during illumination by each of said plurality of beams; and
d) performing a weighted combination of a plurality of said radiographic images to produce a single image.

50. The method of claim 49 wherein said plurality of beams are monoenergetic.

51. The method of claim 49 wherein said plurality of beams are quasi-monoenergetic.

52. The system of claim 49 wherein 2 beams are generated.

53. The system of claim 49 wherein more than 2 beams are generated.

54. The method of claim 49, further displaying variable proportions of radiographic density contributed by said imaging agent, soft tissue, and bone to said single image.

55. The method of claim 48 wherein said intracellular target is a cellular structure.

56. The method of claim 48 wherein said intracellular target is a molecule.

57. The method of claim 48 wherein said intracellular target is selected from the group consisting of proteins, nucleic acids, coenzymes, and lipids.

58. The method of claim 48 wherein said intracellular target is an enzyme.

59. The method of claim 48 wherein said intracellular target is hexokinase.

60. The method of claim 48 wherein said imaging agent accumulates in malignant tissue at a different rate than in non-malignant tissue.

61. The system of claim 48 wherein said imaging agent accumulates in abnormal myocardial tissue at a different rate than in normal myocardial tissue.

62. The method of claim 48 wherein said imaging agent has a logP of above 0.0.

63. A method for generating a functional image and an anatomical image of live tissue in registration comprising:
a) administering to a live organism a radio-opaque imaging agent;
b) generating a plurality of X-ray beams with predetermined different energy spectra;
c) illuminating said live tissue with each of said plurality of beams;
d) acquiring a radiographic image of said live tissue during illumination by each of said plurality of beams;
e) generating said functional image from at least two of said radiographic images.

64. The method of claim 63 wherein said radio-opaque imaging agent comprises a composition having a general formula S-L-X, wherein said composition is cell membrane-permeable and wherein:
S is a binding moiety which selectively binds to a cellular molecule;
X is a radio-opaque moiety; and
L is a linking moiety which links the S moiety to the X moiety.

65. A computer-readable storage medium containing executable computer instructions which, when executed by an image processing system, cause said image processing system to perform a method comprising:
a) acquiring a plurality of radiographic images, wherein each of said radiographic images is acquired during transillumination of live tissue in a living organism by one of a plurality of X-ray beams with a predetermined unique energy spectrum, said living organism having been administered a radio-opaque imaging agent; and
b) generating a functional image from said plurality of radiographic images.

66. A computer-readable storage medium as in claim 65 wherein said method further comprises:
a) displaying said functional image; and
b) displaying one of said plurality of radiographic images which is an anatomical image.

67. A computer-readable storage medium as in claim 66 wherein said functional image and said anatomical image are displayed simultaneously and in aligned registration.

68. A computer-readable storage medium as in claim 66 wherein said functional image and said anatomical image are displayed separately.

69. A computer-readable storage medium containing executable computer program instructions which, when executed by a image processing system, cause said image processing system to perform a method comprising:

a) acquiring at least one radiographic image obtained by irradiating tissue in a living organism with a radiation source which is capable of being attenuated by a composition which is administered to said living organism, wherein said composition is bidirectionally cell membrane-permeable and radio-opaque and capable of binding to a cellular target; and b) generating an image from at least one of said radiographic images.

70. A computer-readable storage medium as in claim 69 wherein said method further comprises displaying said image which is a functional image.

71. A computer-readable storage medium as in claim 69 wherein said method further comprises displaying a radiographic image which is an anatomical image and which is in registration with a functional image.

72. A medium as in claim 65, wherein said functional image indicates the presence or absence of a molecular target.

73. A medium as in claim 65, wherein said functional image indicates the presence or absence of a cellular target.

74. A medium as in claim 65, wherein said functional image indicates the concentration of a cellular target.

75. A method as in claim 63, wherein said functional image indicates the presence or absence of a molecular target.

76. A method as in claim 63, wherein said functional image indicates the presence or absence of a cellular target.

77. A method as in claim 63, wherein said functional image indicates the concentration of a cellular target.

* * * * *